(12) United States Patent
Sharma et al.

(10) Patent No.: US 10,806,928 B2
(45) Date of Patent: Oct. 20, 2020

(54) AURICULAR NERVE STIMULATION TO ADDRESS PATIENT DISORDERS, AND ASSOCIATED SYSTEMS AND METHODS

(71) Applicant: Vorso Corp., Redwood City, CA (US)

(72) Inventors: Vivek K. Sharma, San Ramon, CA (US); Konstantinos Alataris, Menlo Park, CA (US); Gary Heit, Redwood City, CA (US); Jason Sutor, Pacific Grove, CA (US); Pankaj Sunkeri, Belmont, CA (US)

(73) Assignee: Vorso Corp., Redwood City, CA (US)

( * ) Notice: Subject to any disclaimer, the term of this patent is extended or adjusted under 35 U.S.C. 154(b) by 0 days.

(21) Appl. No.: 16/818,977

(22) Filed: Mar. 13, 2020

(65) Prior Publication Data

US 2020/0215327 A1    Jul. 9, 2020

Related U.S. Application Data

(63) Continuation of application No. 16/581,139, filed on Sep. 24, 2019.

(60) Provisional application No. 62/891,203, filed on Aug. 23, 2019, provisional application No. 62/785,205, filed on Dec. 26, 2018, provisional application No. 62/735,492, filed on Sep. 24, 2018.

(51) Int. Cl.
*A61N 1/36* (2006.01)
*A61N 1/04* (2006.01)

(52) U.S. Cl.
CPC ....... *A61N 1/36034* (2017.08); *A61N 1/0456* (2013.01); *A61N 1/36021* (2013.01); *A61N 1/36025* (2013.01); *A61N 1/36036* (2017.08)

(58) Field of Classification Search
CPC .................................................. A61N 1/36036
See application file for complete search history.

(56) References Cited

U.S. PATENT DOCUMENTS

| 4,702,254 A | 10/1987 | Zabara |
| 4,867,164 A | 9/1989 | Zabara |

(Continued)

FOREIGN PATENT DOCUMENTS

WO    WO2018039467    3/2018

OTHER PUBLICATIONS

ISA, PCT Application No. PCTUS2019/052699, International Search Report and Written Opinion dated Dec. 2, 2019, 21 pages.
U.S. Appl. No. 16/723,833, filed Dec. 20, 2019, Alataris et al.

*Primary Examiner* — Michael W Kahelin
(74) *Attorney, Agent, or Firm* — Perkins Coie LLP

(57) ABSTRACT

Auricular nerve stimulation techniques for addressing patient disorders, and associated systems and methods. A representative system includes a signal generator having instructions to generate an electrical therapy signal, at least a portion of the electrical therapy signal having a frequency at or above the patient's auditory frequency limit, an amplitude in an amplitude range from about 0.1 mA to about 10 mA, and a pulse width in a pulse width range from 5 microseconds to 30 microseconds. The system further includes at least one earpiece having a contoured outer surface shaped to fit against the skin of the patient's external ear, external ear canal, or both, the at least one earpiece carrying at least two transcutaneous electrodes positioned to be in electrical communication with the auricular innervation of the patient, e.g., the auricular vagal nerve.

27 Claims, 15 Drawing Sheets

(56) References Cited

U.S. PATENT DOCUMENTS

| | | |
|---|---|---|
| 5,025,807 A | 6/1991 | Zabara |
| 5,215,086 A | 6/1993 | Terry, Jr. et al. |
| 5,231,988 A | 8/1993 | Wernicke et al. |
| 5,263,480 A | 11/1993 | Wernicke et al. |
| 5,269,303 A | 12/1993 | Wernicke et al. |
| 5,299,569 A | 4/1994 | Wernicke et al. |
| 5,330,515 A | 7/1994 | Rutecki et al. |
| 5,335,657 A | 8/1994 | Terry, Jr. et al. |
| 5,458,625 A | 10/1995 | Kendall |
| 5,540,730 A | 7/1996 | Terry, Jr. et al. |
| 5,707,400 A | 1/1998 | Terry, Jr. et al. |
| 5,713,923 A | 2/1998 | Ward et al. |
| 6,587,719 B1 | 7/2003 | Barrett et al. |
| 6,610,713 B2 | 8/2003 | Tracey |
| 6,622,041 B2 | 9/2003 | Terry, Jr. et al. |
| 7,167,750 B2 | 1/2007 | Knudson et al. |
| 7,346,395 B2 | 3/2008 | Lozano et al. |
| 7,784,583 B1 | 8/2010 | Hall et al. |
| 7,797,042 B2 | 9/2010 | Dietrich et al. |
| 8,108,047 B2 | 1/2012 | Schumann |
| 8,391,970 B2 | 3/2013 | Tracey et al. |
| 8,509,905 B2 | 8/2013 | Alataris et al. |
| 8,615,309 B2 | 12/2013 | Craig |
| 8,666,502 B2 | 4/2014 | Hartlep et al. |
| 8,688,239 B2 | 4/2014 | Hartlep et al. |
| 8,729,129 B2 | 5/2014 | Tracey et al. |
| 8,774,926 B2 | 7/2014 | Alataris et al. |
| 8,885,861 B2 | 11/2014 | Beck et al. |
| 8,892,207 B2 | 11/2014 | Nelson et al. |
| 8,914,114 B2 | 12/2014 | Tracey et al. |
| 9,179,222 B2 | 11/2015 | Hillbratt et al. |
| 9,211,409 B2 | 12/2015 | Tracey et al. |
| 9,339,641 B2 | 5/2016 | Rajguru et al. |
| 9,415,220 B1 | 8/2016 | Spinelli et al. |
| 9,662,490 B2 | 5/2017 | Tracey et al. |
| 9,861,816 B2 | 1/2018 | Southwell et al. |
| 10,010,479 B2 | 7/2018 | Brown et al. |
| 10,258,796 B2 | 4/2019 | Alataris et al. |
| 10,493,277 B2 | 12/2019 | Thacker et al. |
| 10,603,494 B2 | 3/2020 | Alataris et al. |
| 2002/0090099 A1 | 7/2002 | Hwang |
| 2006/0100672 A1 | 5/2006 | Litvak |
| 2006/0122675 A1 | 6/2006 | Libbus et al. |
| 2006/0178703 A1 | 8/2006 | Huston et al. |
| 2007/0250145 A1 | 10/2007 | Kraus et al. |
| 2008/0082153 A1 | 4/2008 | Gadsby et al. |
| 2010/0057154 A1 | 3/2010 | Dietrich et al. |
| 2011/0125203 A1 | 5/2011 | Simon et al. |
| 2011/0238141 A1 | 8/2011 | Webb et al. |
| 2013/0079862 A1 | 3/2013 | Ellrich |
| 2014/0206945 A1 | 7/2014 | Liao |
| 2014/0256592 A1 | 9/2014 | Faham |
| 2015/0088212 A1* | 3/2015 | De Ridder ......... A61N 1/36071 607/2 |
| 2015/0165195 A1 | 6/2015 | Hartlep et al. |
| 2016/0022987 A1 | 1/2016 | Zschaeck et al. |
| 2016/0050503 A1 | 2/2016 | Naether |
| 2016/0096016 A1 | 4/2016 | Tracey et al. |
| 2017/0043160 A1* | 2/2017 | Goodall ............... A61B 5/0402 |
| 2017/0368329 A1* | 12/2017 | Tyler ................. A61N 1/36036 |
| 2020/0094054 A1 | 7/2020 | Sharma et al. |

\* cited by examiner

AURICULAR NERVE STIMULATION TO ADDRESS PATIENT DISORDERS, AND ASSOCIATED SYSTEMS AND METHODS

CROSS-REFERENCE TO RELATED APPLICATIONS

The present application is a continuation application of U.S. application Ser. No. 16/581,139, filed Sep. 24, 2019, which claims priority to the following U.S. Provisional Applications 62/735,492, filed on Sep. 24, 2018; 62/785,205, filed on Dec. 26, 2018; and 62/891,203, filed on Aug. 23, 2019. Each of the foregoing applications is incorporated herein in its entirety by reference.

TECHNICAL FIELD

The present technology is directed generally to auricular nerve stimulation techniques for addressing patient disorders, and associated systems and methods.

BACKGROUND

Electrical energy application ("electrical stimulation") to nerves or other neural tissue for the treatment of medical conditions has been used for many decades. Cardiac pacemakers are one of the earliest and most widespread examples of electrical stimulation to treat medical conditions, with wearable pacemakers dating from the late 1950s and early 1960s. In addition, electrical stimulation has been applied to the spinal cord and peripheral nerves, including the vagal nerve. More specifically, electrical stimulation has been applied transcutaneously to the vagal nerves to address various patient indications. While such stimulation has provided successful patient outcomes in at least some instances, there remains a need for improved systems for delivery of transcutaneous vagus nerve stimulation that are compact, light, comfortable for the patient, without stimulation-induced perceptions, consistently positionable in the same location, and able to consistently deliver electrical current over a relatively wide area to accommodate anatomical differences.

BRIEF DESCRIPTION OF THE DRAWINGS

FIGS. 10A-10C illustrate a technique for manufacturing an electrode to provide auricular stimulation in accordance with representative embodiments of the present technology.

DETAILED DESCRIPTION

Figure 1:
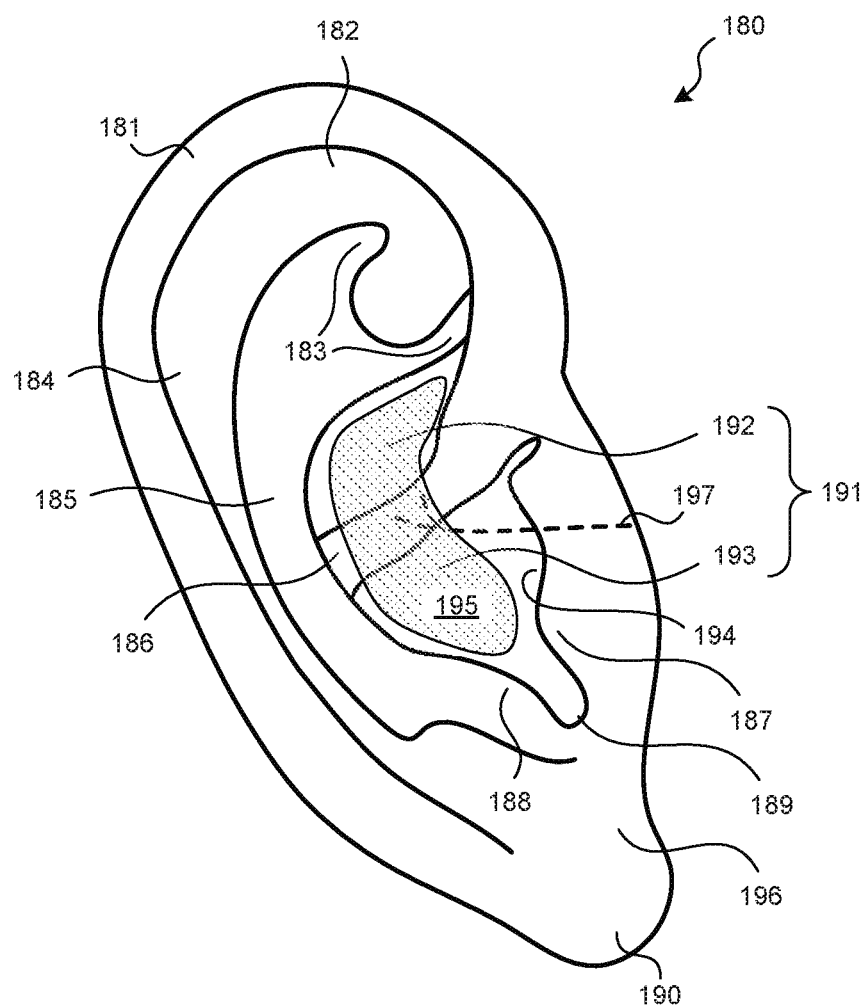
FIG. 1 is a partially schematic side view of a human ear, illustrating a representative target region for stimulation in accordance with embodiments of the present technology.

General aspects of the anatomical and physiological environment in which the disclosed technology operates are described under Heading 1.0 ("Introduction") below. Definitions of selected terms are provided under Heading 2.0 ("Definitions"). Representative treatment systems and their characteristics are described under Heading 3.0 ("Representative Systems"). Representative signal delivery parameters are described under Heading 4.0, representative indications and effects are described under Heading 5.0, representative clinical evaluations are described under Heading 6.0, representative pharmacological supplements are described under Heading 7.0, and further representative embodiments are described under Heading 8.0.

1.0 Introduction

The present technology is directed generally to auricular nerve stimulation to address patient disorders, and associated systems and methods. In particular embodiments, electrical signals are delivered to the auricular branches of the vagal nerve transcutaneously to address any of a variety of patient disorders, including for, example rheumatoid arthritis, migraine headache, and asthma. Further disorders treatable by these techniques are described later herein. The electrical signals are generally provided at frequencies ranging from about 15 kHz to about 50 kHz. In particular embodiments, the frequency of the signal is selected to be above the patient's auditory limit, so as to avoid inducing potentially unwanted side effects via the patient's hearing faculties. In further representative embodiments the physiological location to which the electrical signals are delivered is deliberately selected to generate primarily or exclusively afferent signals. Accordingly, the effect of the stimulation can be limited to reducing the effects and/or the underlying causes of the patient disorder, via stimulation that targets particular brain regions, without the signals inadvertently stimulating other (e.g., peripheral) nerves of the patient.

2.0 Definitions

Unless otherwise stated, the terms "about" and "approximately" refer to values within 20% of a stated value.

As used herein, and unless otherwise noted, the terms "modulate," "modulation," "stimulate," and "stimulation" refer generally to signals that have an inhibitory, excitatory, and/or other effect on a target neural population. Accordingly, a "stimulator," "electrical stimulation" and "electrical therapy signals" can have any of the foregoing effects on certain neural populations, via electrical communication (e.g., interaction) with the target neural population(s).

As used herein, the term "auricular nerve" includes the auricular branch of the vagal nerve (sometimes referred to as Arnold's nerve or aVN), as well as other auricular nerves, for example, the greater auricular nerve, and/or the trigeminal nerve.

The term "therapeutically-effective amount," as used herein, refers to the amount of a biologically active agent needed to initiate and/or maintain the desired beneficial result. The amount of the biologically active agent employed will be that amount necessary to achieve the desired result. In practice, this will vary widely depending upon the particular biologically active agent being delivered, the site of delivery, and the dissolution and release kinetics for delivery of the biologically active agent (including whether the agent is delivered topically, orally, and/or in another manner), and the patient's individual response to dosing.

The term "paresthesia" refers generally to an induced sensation of numbness, tingling, prickling ("pins and needles"), burning, skin crawling, and/or itchiness.

Several aspects of the technology are embodied in computing devices, e.g., programmed/programmable pulse generators, controllers and/or other devices. The computing devices on/in which the described technology can be implemented may include one or more central processing units, memory, input devices (e.g., input ports), output devices (e.g., display devices), storage devices, and network devices (e.g., network interfaces). The memory and storage devices are computer-readable media that may store instructions that implement the technology. In some embodiments, the computer- (or machine-) readable media are tangible media. In some embodiments, the data structures and message structures may be stored or transmitted via an intangible data transmission medium, such as a signal on a communications link. Various suitable communications links may be used, including but not limited to a local area network and/or a wide-area network.

3.0 Representative Systems

Representative systems in accordance with the present technology deliver electrical signals transcutaneously to the auricular branch(es) of a patient's vagus nerve. The signals are delivered via electrodes positioned at or partially within one or both of the patient's ears. FIG. 1 illustrates the general physiology of the external portion of a human ear 180, indicating a representative target region 195 at which the electrical signals are applied. The external ear 180 includes the helix 181 partially encircling the triangular fossa 182 and the scaphoid fossa 184, and terminating at the lobule or lobe 190. Within the helix 181 is positioned the antihelix 185, the antihelix crura 183, the antitragus 188, and the intertragic notch 189. The concha 191 is positioned inwardly from the antihelix 185, and includes the cymba concha 192 and cavum concha 193, bounded by the tragus 187 and separated from the cymba concha 192 by the helix crus 186. The skin 196 of the external ear 180 extends into the external ear canal 194, which terminates at the ear drum (not visible in FIG. 1). The auricular branch of the vagus nerve 197 innervates the ear 180, and the target region 195 is generally over and/or adjacent the auricular branch 197.

As shown in FIG. 1, the target region 195 is positioned primarily at the concha 191 and can extend at least partially into the ear canal 194. Devices configured in accordance with embodiments of the present technology are configured not only to deliver electrical therapy signals to the target region 195, but to provide a comfortable, repeatable, and in at least some embodiments, patient-specific, structures and therapy signals for doing so.

Figure 2:
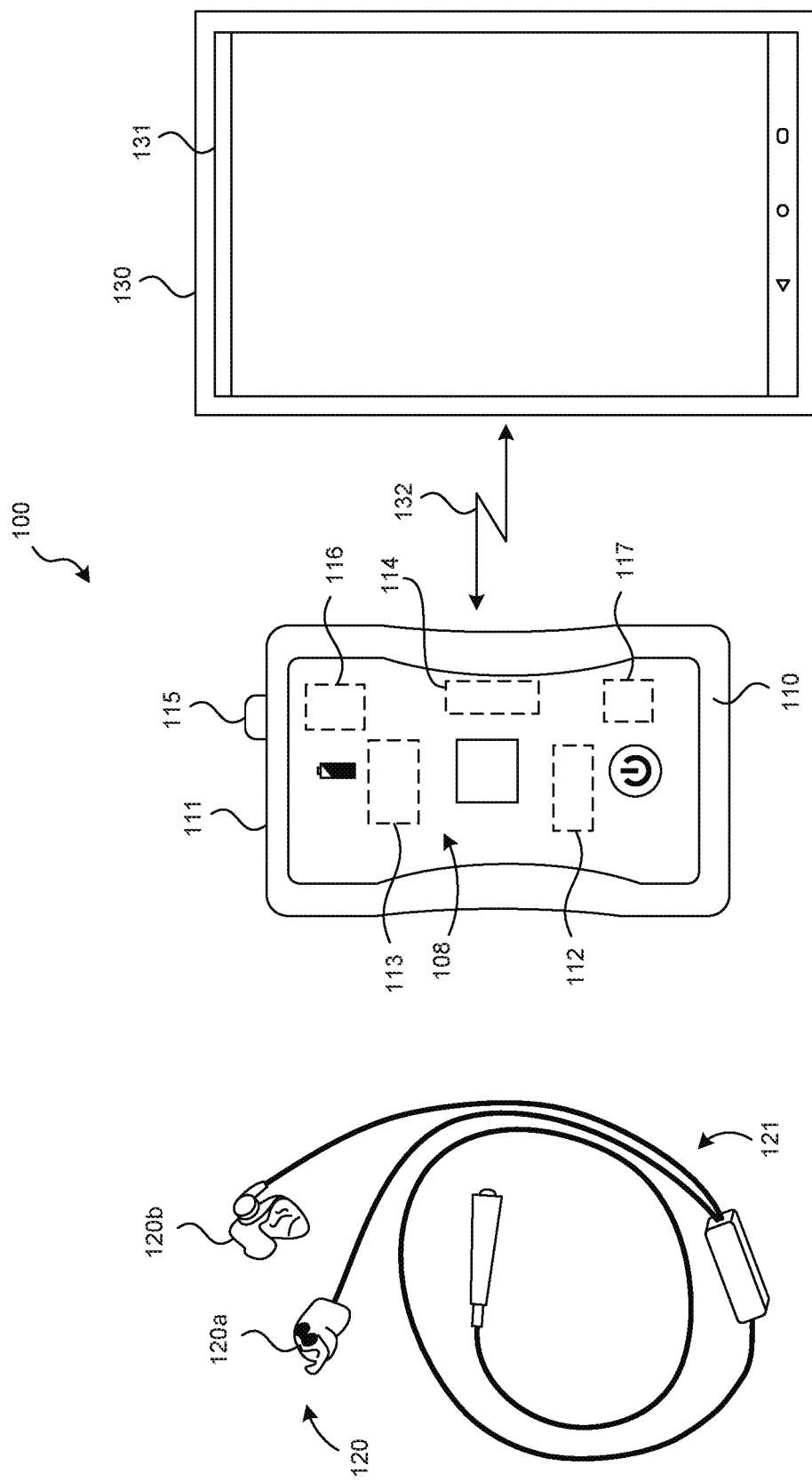
FIG. 2 is a partially schematic illustration of a system having earpieces, a signal generator, and an external controller arranged in accordance with representative embodiments of the present technology.

FIG. 2 is a partially schematic illustration of a representative system 100 for transcutaneously delivering electrical therapy signals to the auricular branches of the patient's vagus nerves, in accordance with representative embodiments of the present technology. The system 100 includes a signal generator 110 coupled to one or more earpieces 120 (shown as a left earpiece 120a and a right earpiece 120b), and an external controller 130. The signal generator 110 can include a housing 111 that encloses or partially encloses signal generating circuitry 114. The signal generating circuitry 114 can be controlled by an internal controller 108, e.g., a processor 113 that accesses instructions stored in a memory 112. The signal generator 110 can include a signal transmission port 115 for communicating with the earpieces 120, e.g., transmitting an electrical therapy signal to the earpieces 120, and optionally, receiving feedback or other communications from the earpieces 120. When the system 100 is in use, the electrical therapy signal is in electrical communication with the target neural population to create a desired effect on the target neural population. A communications transceiver 116 provides for communication between the signal generator 110 and the external controller 130.

The earpieces 120 can be coupled to the signal generator 110 via one or more earpiece links 121. In particular embodiments, the earpiece link 121 includes a wired link e.g., a cable or other elongated conductor. In other embodiments, the earpiece link 121 can include a wireless connection. The earpiece link or links 121 can be connected to each of the earpieces 120 to provide the same input to each, or differentiated inputs to each. The earpiece link(s) 121 can also direct communications (e.g., patient data) back to the signal generator 110, e.g., from sensors carried by the earpieces 120.

The signal generator 110 can be configured to rest on any suitable surface (e.g., a table top), or can be carried by the patient in the patient's hand or in a holster or in another suitable manner. The signal generator 110 can be powered by a power source 117, e.g., one or more batteries (e.g., rechargeable batteries) and/or an external power source. In particular embodiments, the signal generator 110 is controlled by the external controller 130 via a controller link 132. The external controller 130 can include a cellular phone or other mobile device (e.g., a smartwatch), and can access a specific phone-based app 131 to provide controls to the signal generator 110. In operation, a physician or other suitable practitioner can set the stimulation parameters at the signal generator 110 via the external controller 130, and the patient and/or the practitioner can update the signal delivery parameters via the same or a different external controller 130. In some embodiments, the practitioner may have control over more parameters than the patient does, for example, to better control possible patient outcomes. The practitioner (and/or others) may direct or otherwise affect the internal controller 108 remotely via the external controller 130 and/or other devices, e.g., a backend device as described further with reference to FIG. 4.

Figure 3A:
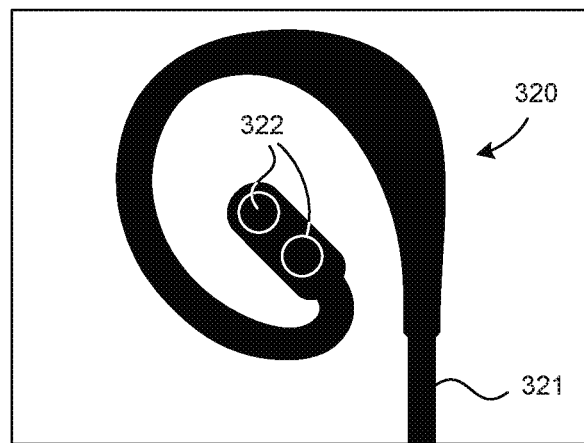
FIGS. 3A and 3B illustrate an earpiece having electrodes positioned to apply stimulation in a clinical setting, in accordance with representative embodiments of the present technology.
Figure 3B:
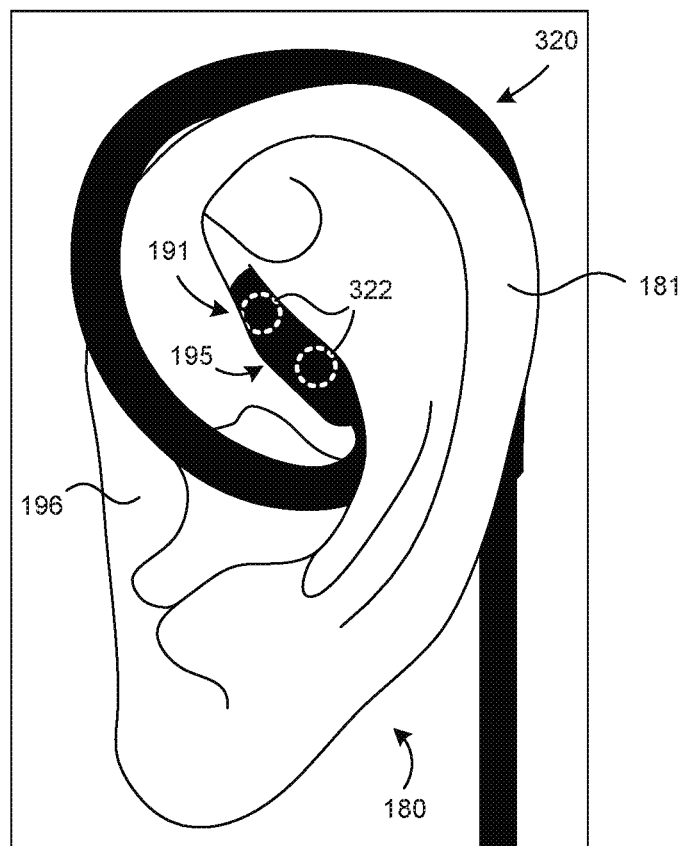

FIGS. 3A and 3B illustrate a representative earpiece 320 by itself (FIG. 3A) and in position on the patient's ear 180 (FIG. 3B). With reference first to FIG. 3A, the earpiece 320 includes two electrodes 322, and an earpiece link 321 for communication with the associated signal generator. The two electrodes 322 are positioned to provide a transcutaneous, bipolar signal to the patient's ear.

Referring next to FIG. 3B, the earpiece 320 is positioned at the patient's ear 180, with a portion of the earpiece 320 extending behind the helix 181 for support, and with the electrodes 322 positioned at the target region 195, e.g., against the patient's skin 196 at the concha 191. This positioning has been demonstrated in a clinical setting to provide effective therapy for the patient. As discussed further below, other earpiece configurations can provide additional positioning precision and/or patient comfort.

Figure 4:
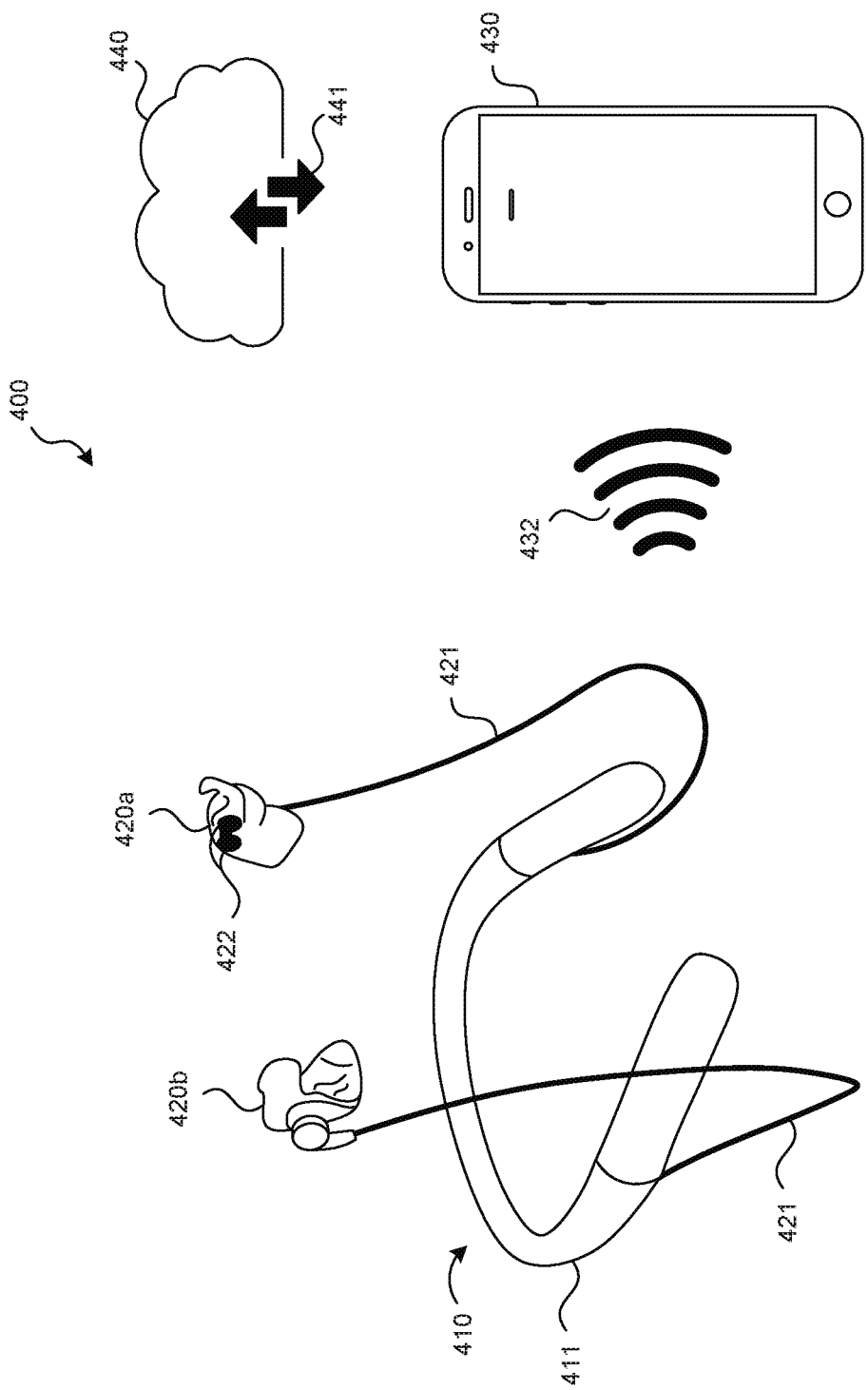
FIG. 4 is a partially schematic illustration of a system having a signal generator positioned within a housing that fits around the patient's neck, in accordance with embodiments of the present technology.

FIG. 4 is a partially schematic illustration of a representative system 400 configured in accordance with the present technology. The system 400 includes a signal generator 410 that has a generally horseshoe-shaped housing 411 so as to fit comfortably around the patient's neck when in use, and may accordingly be referred to herein as a neckpiece. The housing 411 can in turn include the internal components described above with reference to FIG. 2. Two earpiece links 421 (e.g., in the form of flexible cables) connect the signal generator 410 to corresponding earpieces 420a, 420b, which each carry two electrodes 422. The signal generator 410 can be controlled by an external controller 430 via a wireless controller link 432. The external controller 430 can accordingly be used to set and/or adjust the signal delivery parameters in accordance with which the signal generator 410 provides therapeutic electrical signals to the earpieces 420.

The external controller 430 can also communicate with a backend device 440 (e.g., a server or other suitable device located on the cloud or other medium) via a backend link 441. Accordingly, the external controller 430 can exchange data with the backend 440. For example, the external controller 430 can provide the backend 440 with information about the patient's condition (e.g., obtained from feedback sensors included in the system 400), and/or a schedule of the signal delivery parameters selected by the patient or practitioner over the course of time. In addition, (or alternatively), the backend 440 can be used to provide updates to the phone-based app or other software contained on the external controller 430. The allocation of processing tasks and/or data storage between the internal controller 108 (FIG. 2), the external controller 430 and the backend 440 can be selected to suit the preferences of the patient, practitioner, and/or others.

Figure 5A:
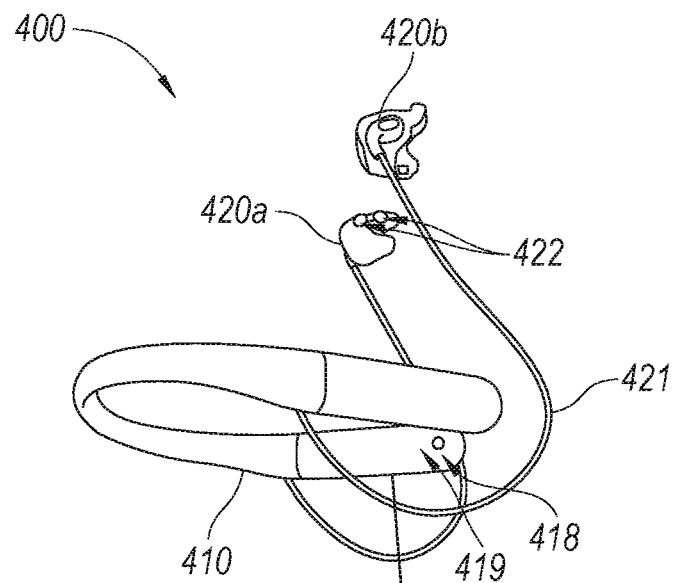
FIGS. 5A and 5B are further illustrations of portions of the representative system shown in FIG. 4.
Figure 5B:
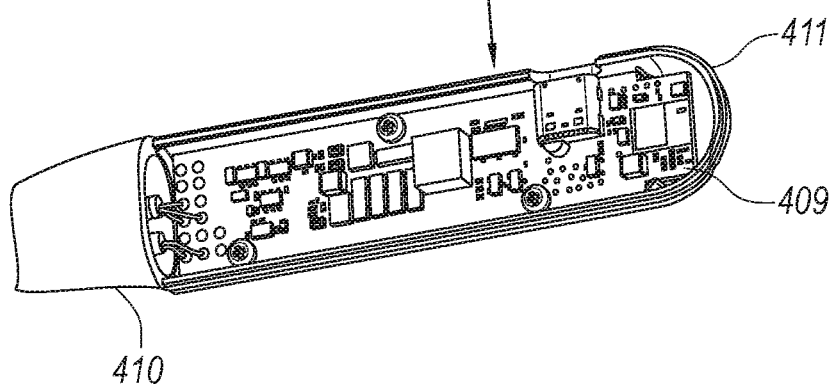

FIGS. 5A and 5B further illustrate features of the system 400 described above with reference to FIG. 4. In particular, FIG. 5A illustrates the signal generator 410 as including an input device 418 and an output device 419. The input device 418 can include a button or other element to activate or deactivate the signal generator 410. The output device 419 can include an LED or other element to indicate when the signal generator 410 is on. In other embodiments, the input device 418 and/or the output device 419 can be used to perform other suitable functions. For example, the output device 419 can provide an audible tone or other alert if the earpiece(s) 120 are not correctly positioned. The input device 418 can accept user inputs (as described above), or can be a sensor, e.g., a proximity sensor that detects contact with the patient's skin, via an impedance measurement or otherwise and is coupled to the output device 419 to provide the alert. The frequency of the alert tone can be patient-specific because, as described later, different patients may have different hearing ranges.

FIG. 5B schematically illustrates a portion of the signal generator 410, with part of the housing 411 cut away to illustrate a printed circuit board 409. The printed circuit board 409 can carry the internal components described above with reference to FIG. 2, and is coupled to the earpiece link 421.

Figure 6A:
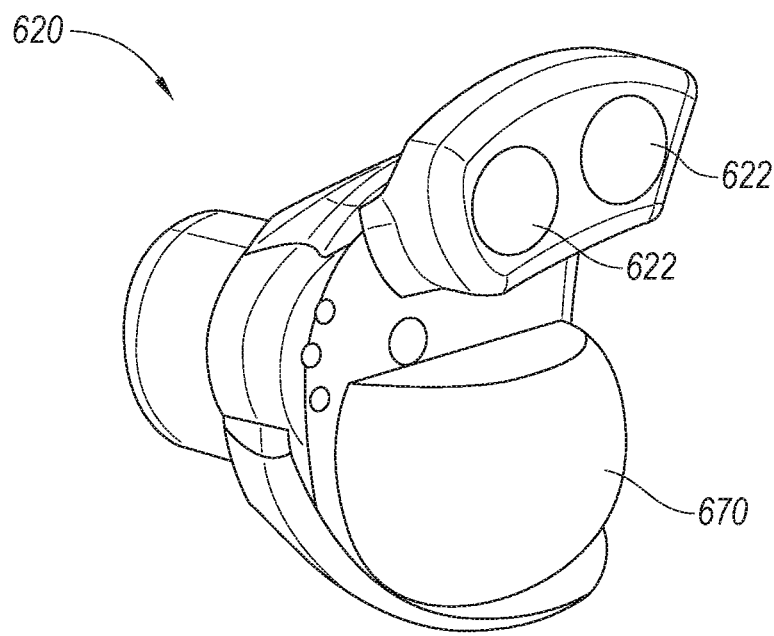
FIGS. 6A and 6B are partially schematic isometric illustrations of an earpiece carrying two electrodes in accordance with representative embodiments of the present technology.
Figure 6B:
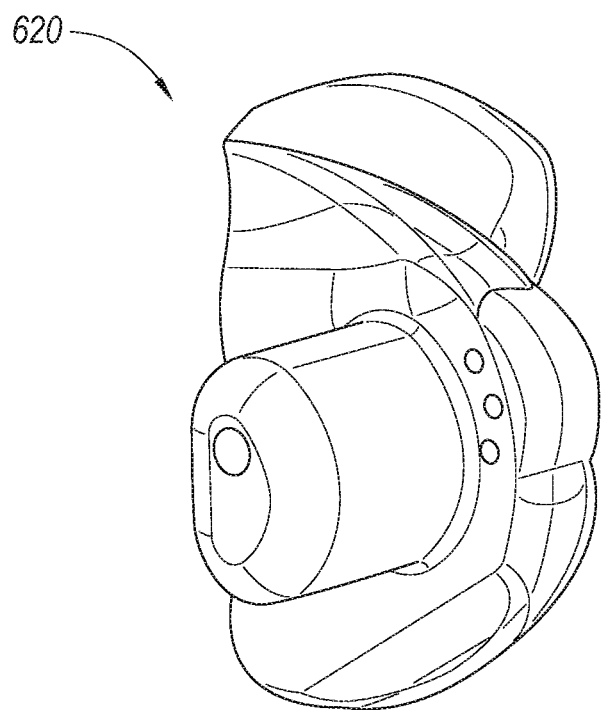

FIGS. 6A and 6B illustrate front and rear views, respectively, of a representative earpiece 620 configured to fit a variety of patient physiologies. The earpiece 620 includes two electrodes 622 positioned to provide transcutaneous stimulation to the target region 195 (FIG. 1). In addition, the earpiece 620 includes features configured to provide for patient comfort and to securely, yet removably, keep the electrodes 622 in position at the target region. For example, the earpiece 620 can include a bulging, flexible portion 670 that provides for snug contact between the electrodes 622 and the patient's skin at the target region. This approach can make device placement more consistent and repeatable across a patient population.

The earpieces shown in FIGS. 6A and 6B, as well as elsewhere herein, may be fungible items that are replaced periodically due to normal wear. Accordingly, the earpieces can be configured to separate from the rest of the system for replacement.

Figure 7:
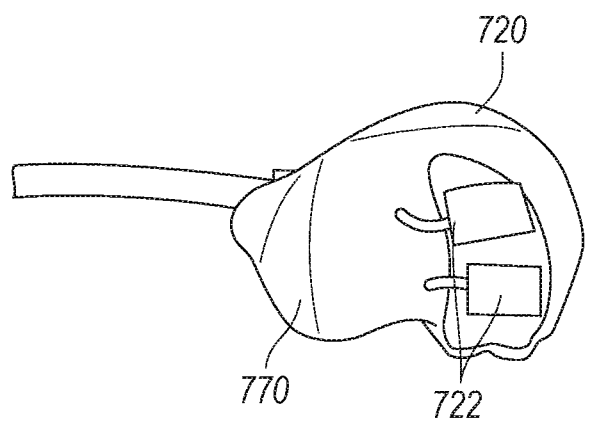
FIG. 7 is a partially schematic illustration of an earpiece that includes custom-fit components in accordance with embodiments of the present technology.

FIG. 7 illustrates another representative earpiece 720 having electrodes 722. As shown in FIG. 7, the electrodes 722 can have a shape other than the circular shape shown in FIGS. 6A and 6B. For example, the electrodes 722 can have a rectangular shape. In other embodiments, the electrode 722 can have an ovoid shape or other shape that is specific to one or more patients, e.g., based on patient physiology.

In at least some embodiments, the earpiece 720 shown in FIG. 7 can be custom-made to fit a particular patient. For example, comparing the earpiece 720 shown in FIG. 7 with the earpiece 620 shown in FIG. 6A, it is evident that the flexible portion 770 of the custom-made earpiece 720 is larger and bulges outwardly more than the corresponding flexible portion 670 shown in FIG. 6A. The custom earpiece 720 can accordingly fit better in the particular patient's ear. Representative techniques for forming the earpiece 720 can include making a mold of the patient's ear and, for at least a portion of the earpiece, duplicating the contours of the mold so as to fit in the patient's ear. In other embodiments, many of the processes can be performed digitally, e.g., using 3-D imaging techniques to identify the contours of the patient's ear, and 3-D additive manufacturing techniques or computer-controlled subtractive manufacturing techniques to form the earpiece contours. The earpiece may be constructed from materials that are soft and moldable (e.g., 10-60 on the Shore A hardness scale). Accordingly, the earpiece can form a tight and/or "snug" fit in the patient's ear to position the electrodes at the target region (e.g., the concha, and in particular cases, the cymba concha). In some embodiments, the custom fit may be achieved via moldable plastic materials. In other embodiments, the custom fit may be achieved by the use of materials with appropriate stickiness of tackiness that can mold to and remain tightly and snug on the outer area of the patient's ear and target the concha without the discomfort or suboptimal connections found in devices that can only be secured by entering the ear canal. The conformal nature of the earpiece can produce an electrode-to-skin contact area in a range of from 20% to 100% of the exposed electrode surface area. This intimate contact can further reduce the likelihood for generating paresthesia, because less energy is required to be delivered to the electrode to achieve a therapeutic effect.

An advantage of a custom earpiece is that it is likely to be more comfortable and/or provide more effective therapy than a standard-size earpiece. Conversely, the standard-sized earpiece is likely to be less expensive to manufacture. Accordingly, in some instances, patients and practitioners can use standard earpieces where practical, and custom earpieces as needed.

Figure 8A:
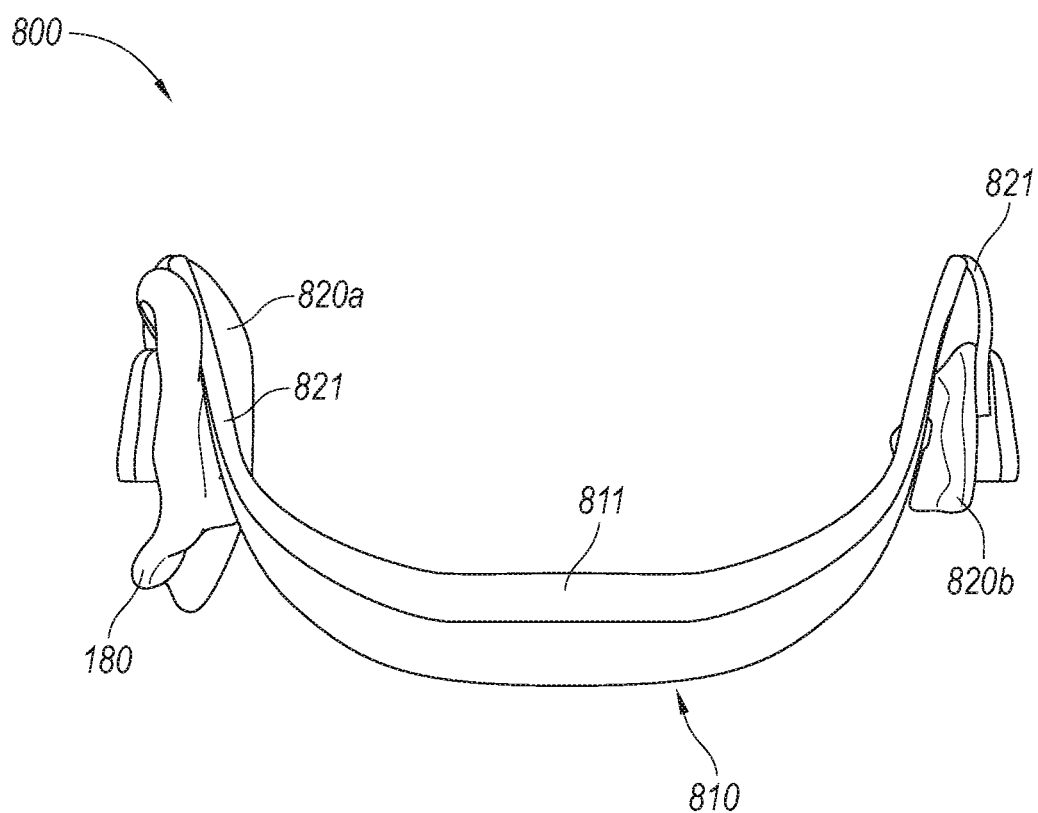
FIGS. 8A and 8B are partially schematic rear and side views, respectively, of a system having a signal generator integrated with two earpieces, in accordance with representative embodiments of the present technology.
Figure 8B:
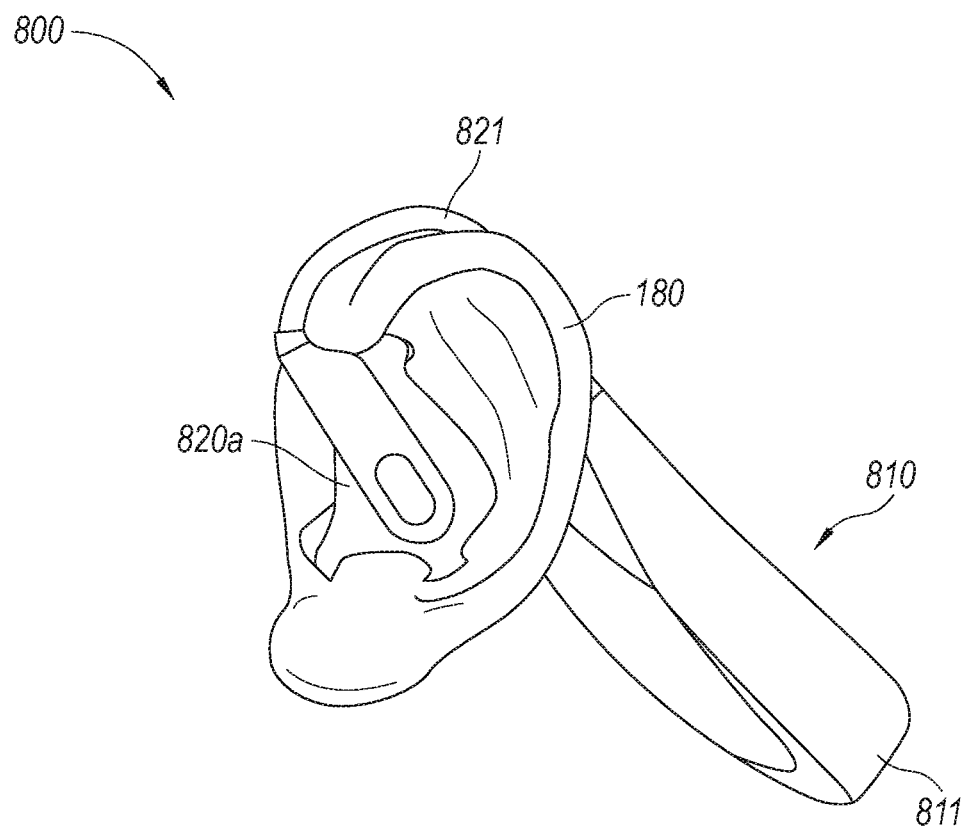

FIGS. 8A and 8B illustrate another representative system 800 having a signal generator 810, earpieces 820a, 820b, and earpiece links 821, all of which are integrated to provide a unitary, single-piece device. For example, the signal generator 810 can include a housing 811 that houses the earpiece links 821 (in addition to the signal generating circuitry), and directly supports the earpieces 820a, 820b. In particular embodiments, the earpieces 820a, 820b can be removable from the housing 811 for periodic replacement (as discussed above), but the housing 811 can nevertheless provide a more robust support for the earpieces than the flexible cable described above with reference to FIG. 2. Whether the patient uses a one-piece configuration as shown in FIGS. 8A and 8B, or other configurations shown herein, can depend on patient preferences, and the degree to which the system provides consistent, effective treatment for the particular patient.

Figure 9A:
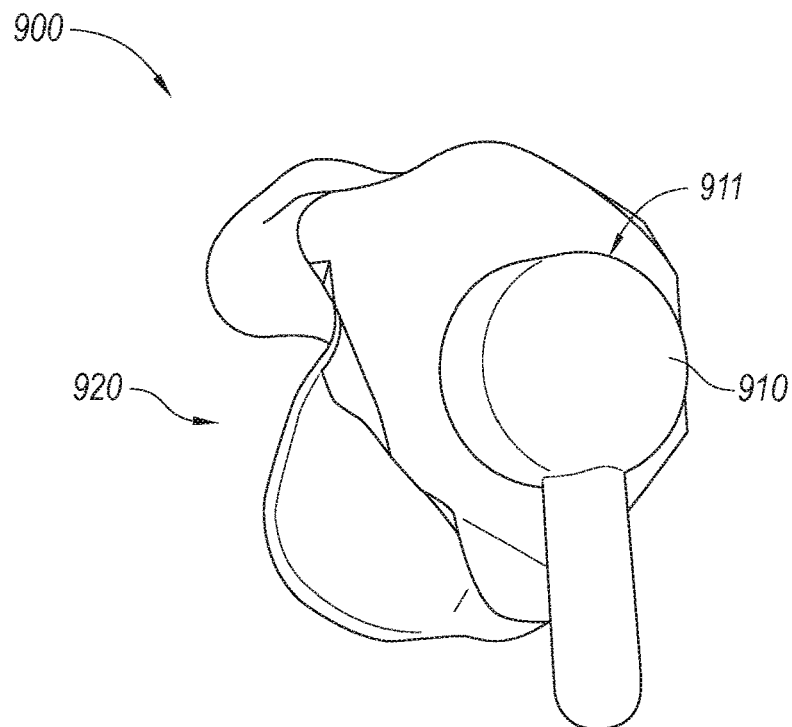
FIGS. 9A and 9B illustrate a system that includes multiple earpieces, each with an integrated signal generator, in accordance with embodiments of the present technology.
Figure 9B:
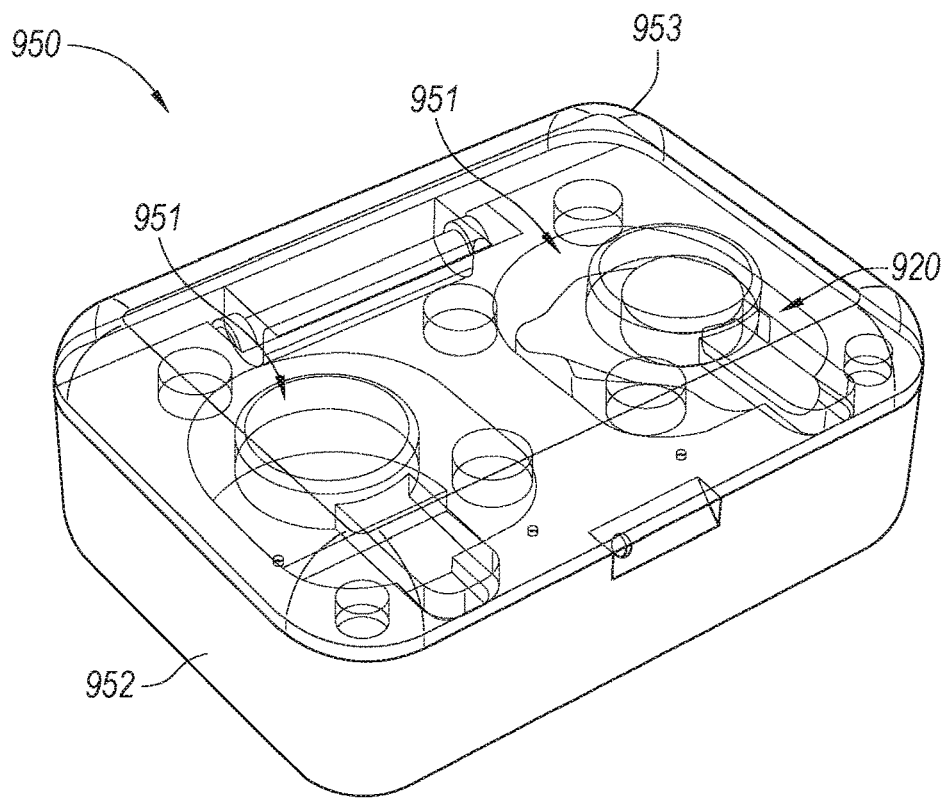

FIGS. 9A and 9B illustrate a further representative system 900 in which the signal generator 910 is integrated with the earpiece 920 in a single housing 911. Beginning with FIG. 9A, for patients using multiple earpieces (as is typical), each earpiece includes a dedicated signal generator 910. In at least some embodiments, the signal generators 910 can communicate with each other (e.g., wirelessly) to provide for consistent treatment. An advantage of the approach shown in FIG. 9A is that it may be more comfortable and/or less cumbersome than devices that have the signal generators positioned some distance away from the earpieces. Conversely, devices with the signal generator positioned away from the earpieces may provide more stability for the earpieces, and/or increased patient comfort.

FIG. 9B illustrates a representative charging station 950 for charging the signal generator 910 shown in FIG. 9A. The charging station 950 can include a base 952 having multiple ports 951 (e.g., one port for each earpiece 920) and an optional cover 953 to protect the earpieces 920 during charging. The earpieces 920 can be charged inductively so as to avoid the need for direct mechanical contact between electrical elements of the signal generator 910 and electrical elements of the charging station 950. The charging station 950 itself can receive power via a conventional wall outlet, battery, and/or other suitable source.

Figure 10C:
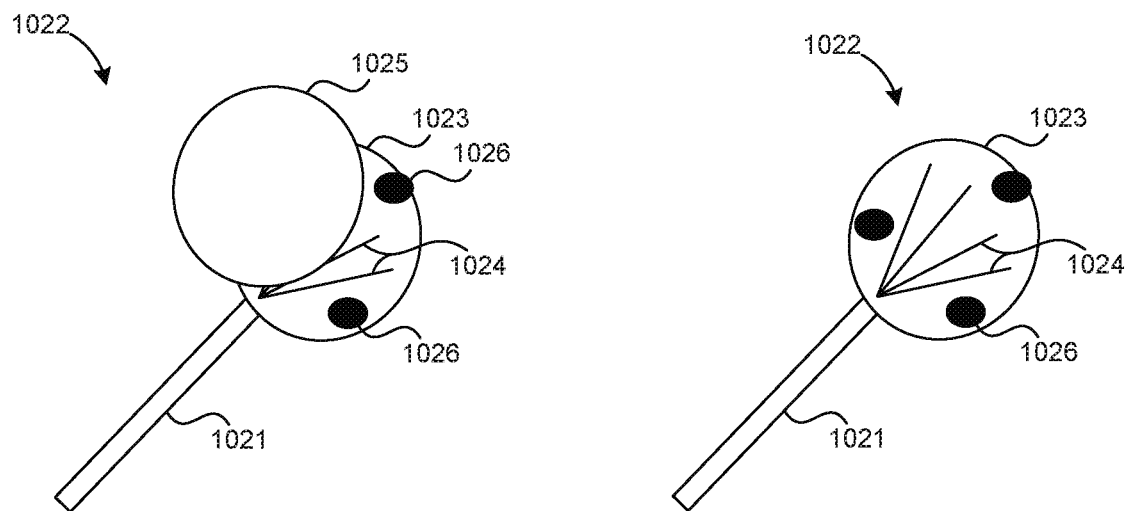
Figure 10C:
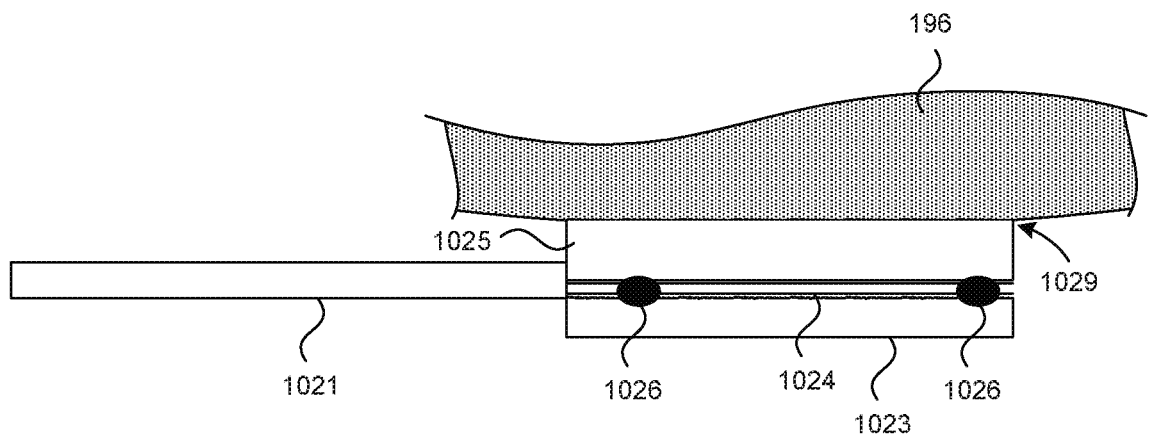

FIGS. 10A-10C illustrate a representative technique for manufacturing electrodes in accordance with embodiments of the present technology. Referring first to FIGS. 10A and 10B a representative electrode 1022 includes a backing 1023, e.g., a fabric and/or textile with an acrylic adhesive, and/or a non-fabric (e.g., vinyl). The earpiece link 1021 can include an insulated conductive wire with individual wire strands 1024 that are spread apart and placed against the backing 1023. Optionally additional adhesive 1026 is then used to secure the wire strands 1024 and backing 1023 to a conductive material 1025 (removed in FIG. 10B) that contacts the patient's skin.

FIG. 10C is a partially schematic, cut-away illustration of the electrode 1022 illustrating the sandwich construction of the backing 1023, the wire strands 1024, and the conductive material 1025. In particular embodiments, the conductive material 1025 can include a conductive silicone and/or other polymer (e.g., a silicone impregnated with one or more conductive materials), which is comfortable to place against the patient's skin 196. During use, the practitioner or patient can brush an electrically conductive solution 1029 on the conductive material 1025. The solution need not be adhesive because the force used to keep the electrode 1022 in place is a mechanical force provided by other portions of the earpiece structure, which are in contact with the patient's skin. The conductive material 1025 can be roughened or otherwise textured so as to retain the solution 1029 for the duration of a treatment period. As discussed in further detail below under Heading 4.0, individual treatment periods are relatively short in duration.

In certain embodiments, the foregoing electrode design and production process allows a user (patient and/or practitioner) to adjust the surface properties to help better retain the solution 1029 between the electrode 1022 and the skin surface (e.g., via roughening, as described above). Further, the design can facilitate tuning the impedance across the electrode surface by arranging the conductor wires (e.g., formed from metal or carbon) in certain shapes. The electrodes described herein may also be designed to reduce current "hotspots" by features in the mold. In some embodiments, the electrode together with the earpiece housing or enclosure can include a built-in mechanism to apply the solution 1029 on the electrode surface before and/or after each use.

The earpiece as a whole can also maintain intimate contact with the skin at its functional surfaces by using features of the patient's ear as a lever, for example, providing intimate electrical contact at the cymba concha by pushing off the inside of the antitragus, or via alignment with the ear canal.

Figure 11A:
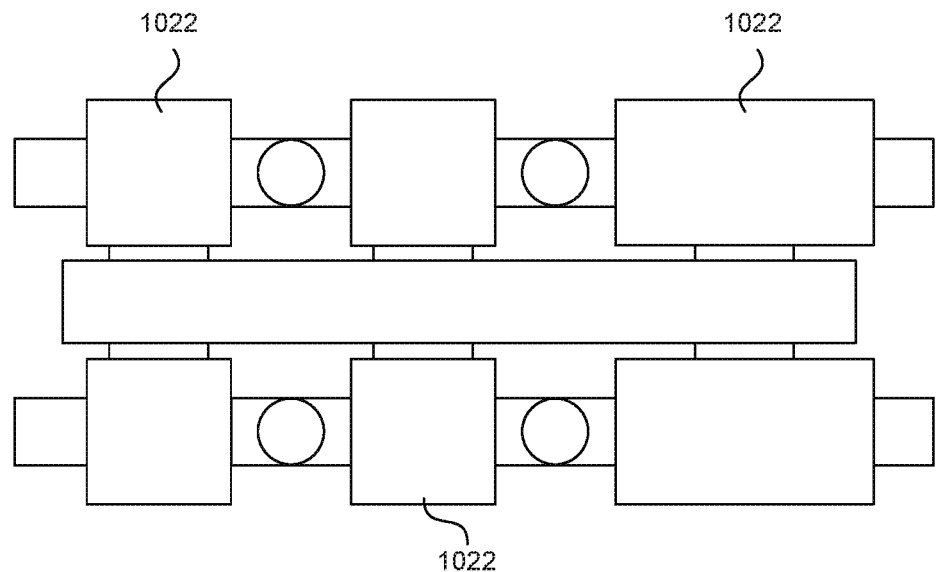
FIGS. 11A-11C illustrate a representative technique for manufacturing larger volumes of electrodes in accordance with representative embodiments of the present technology.
Figure 11B:
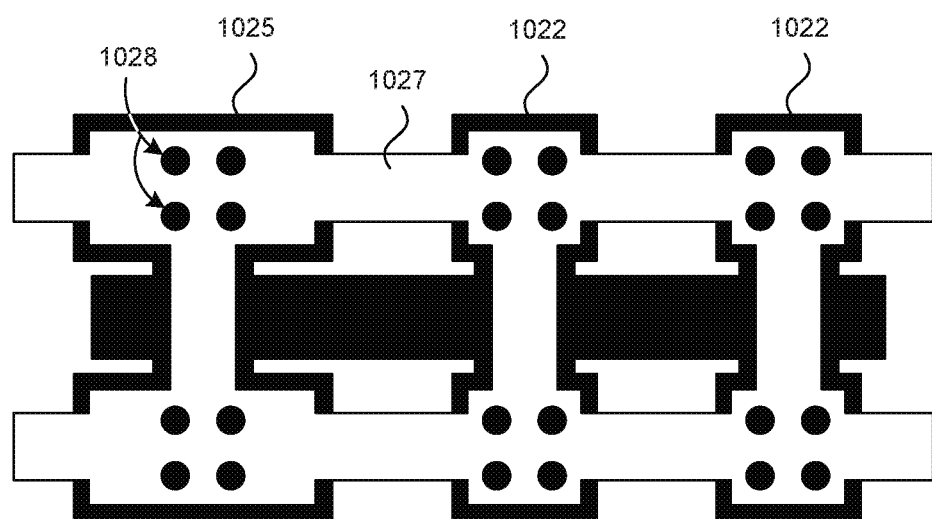
Figure 11C:
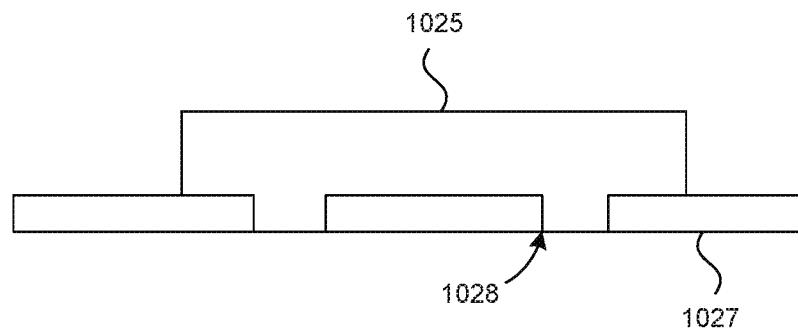

FIGS. 11A-11C illustrate a technique for larger scale production of the electrodes 1022. FIGS. 11A-11C illustrate top, bottom and cross-sectional views, respectively, of an intermediate stage of production in which the conductive material 1025 is positioned against a layer of foil 1027 (not visible in FIG. 11A) so that portions of the conductive material 1025 project through openings 1028 to hold the conductive material 1025 in place. The foil 1027 provides an electrical path to the electrodes 1022. In this embodiment, six (rectangular) electrodes are formed together and then separated prior to installation on corresponding earpieces.

4.0 Representative Signal Delivery Parameters

Figure 12:
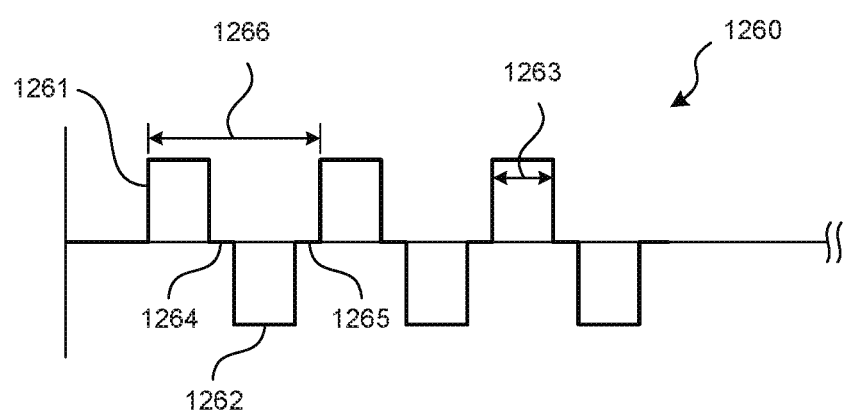
FIG. 12 is a schematic illustration of a representative wave form in accordance with embodiments of the present technology.

The representative systems described above deliver electrical signals to the patient in accordance with selected signal delivery parameters. The signal delivery parameters can include the characteristics defining or describing the signal, and the location to which the signal is delivered. In general, the signal is biphasic and is applied at a frequency in a range of about 15 kHz to about 50 kHz. FIG. 12 is a schematic illustration of a representative signal 1260. The signal (e.g., the signal wave form) includes anodic pulses 1261 and cathodic pulses 1262 separated by an interphase spacing 1264. Individual pairs of anodic and cathodic pulses 1261, 1262 can be separated from neighboring pairs by an interpulse spacing 1265. Each pulse can have a pulse width 1263, which can be the same for anodic pulses 1261 as for cathodic pulses 1262, or different, depending upon the embodiment. The repeating period of the signal 1266 is made up of the anodic pulse 1261, the cathodic pulse 1262, the interphase spacing 1264, and the interpulse spacing 1265. The inverse of the period 1266 corresponds to the frequency of the signal.

In representative embodiments, at least a portion of the signal 1260 has signal delivery parameters in the following ranges:
- Frequency: about 15 kHz to about 50 kHz, or about 20 kHz to about 50 kHz or 20 kHz
- Amplitude: about 0.1 mA to about 10 mA, or about 1 mA to about 5 mA, or about 2 mA to about 4 mA
- Pulse width: about 5 microseconds to about 30 microseconds, e.g., about 20 microseconds
- Interphase spacing: about one to about 10 microseconds
- Interpulse spacing: about one to about 15 microseconds
- Duty cycle: on-period of 0.1 seconds—15 minutes off-period of 0.1 seconds—15 minutes In some embodiments, the signal 1260 (e.g., the values of the foregoing parameters) remain constant for the duration that the signal is delivered. In other embodiments, one or all of the foregoing parameters can vary, with the average value remaining in the foregoing ranges. For example, the frequency can be varied, while the average frequency remains within the foregoing range of about 15 kHz to about 50 kHz. Representative varying waveforms include Gaussian and/or other non-linear waveforms. The average frequency corresponds to the inverse of the average period of the signal taken over multiple periods. As described above, an individual period is the sum of the anodic pulse width (e.g., a first pulse width), the cathodic pulse width (e.g., a second pulse width) of a neighboring pulse, the interphase spacing, and the interpulse spacing.

As described herein, at least a portion of the signal has parameters within the foregoing ranges. Accordingly, in some embodiments, the signal may deviate from the foregoing ranges so long as doing so does not significantly impact the efficacy of the therapy and/or the comfort of the patient.

The electrical therapy signal is typically delivered to the patient over the course of one or more sessions that have a limited duration. For example, an individual session typically lasts no longer than sixty minutes and is typically at least two seconds in duration. In more particular embodiments, the duration ranges from about two seconds to about thirty minutes, and in a further particular embodiment, the duration is from five minutes to twenty minutes, or about fifteen minutes. The patient can receive treatment sessions at most once per day, at most twice per day, or at other suitable intervals, depending, for example, on the patient's response to the therapy. In a representative embodiment, the patient receives therapy in two 15 minute sessions, spaced apart by about 12 hours.

It is expected that electrical therapy signals having parameters in the foregoing ranges will provide effective therapy to the patient, without causing paresthesia and/or other potentially undesirable sensory responses in the patient. Accordingly, the electrical therapy signal may be referred to herein as a non-sensory response therapy signal. Undesirable sensory responses include, in addition to or in lieu of paresthesia, a sensation of heat and/or pressure, and/or side effects related to the patient's hearing faculties. In particular, the frequency of the signal can be deliberately selected to be above the patient's upper hearing threshold. While it is not believed that the therapy signal generates sound waves, it may nevertheless trigger an auditory response, e.g., a sensation of "ringing," possibly through mechanical, bone, and/or far-field electrical conduction, and/or interactions with native mechanical acoustic damping systems, e.g., the tensor tympani muscle. The typical upper hearing threshold for a patient is at or below 15 kHz and accordingly, a signal having a frequency in the range of about 15 kHz to about 50 kHz can provide paresthesia-free stimulation, without triggering auditory effects. Because the upper threshold differs from patient to patient, the signal frequency can be selected on a patient-by-patient basis. For example, patients having a reduced upper threshold (e.g., older patients) can potentially receive a beneficial effect from stimulation toward the lower end of the above frequency range, or even below the above frequency range. The patient's upper auditory threshold may change over time. By customizing the frequency to an individual patient, a wider range of frequencies are available to the practitioner. In addition, lower frequencies may consume less power, which can in turn allow the device applying the stimulation to be smaller, and/or to undergo fewer recharging cycles.

As discussed above, the electrodes applying the stimulation are positioned to target the auricular branches of the patient's vagal nerve. It is expected that, by targeting the auricular branches, the effect of the signals will be limited to an afferent effect (e.g., affecting the brain) and not an efferent effect (e.g., affecting other peripheral nerves). An advantage of this arrangement is that the likelihood for inducing unwanted side effects is limited, and instead, the stimulation is focused on producing an effect on the patient's brain to provide a therapeutic result.

5.0 Representative Indications and Effects

Embodiments of the present technology are suitable for treating a variety of patient indications. Representative indications include: (1) inflammatory indications (e.g., arthritis, rheumatoid arthritis, fibromyalgia, irritable bowel syndrome, Crohn's disease, asthma, psoriasis, Sjogren's Syndrome, autoimmune nephropathy (e.g. Berger's IgA), sepsis, and lupus); (2) neurological indications (e.g., depression, post-partum depression, Alzheimer's disease, migraine, headaches, cluster headaches, epilepsy, and mood disorders); (3) sleep-related indications (e.g., insomnia, failure to achieve deep sleep, REM sleep behavior disorder, and parasomnia; (4) functional enhancement (e.g., memory enhancement, associative learning); and/or (5) pulmonary dysfunctions (asthma, allergic rhinitis, allergic bronchitis, exercise induced bronchoconstriction).

Without bound by theory, it is believed that the efficacy of the presently disclosed therapeutic technique may be correlated with changes in the brain's functioning. In particular, it is expected that networking and/or connectivity between areas of the brain will improve or revert to normal as a result of the therapy. Representative affected areas of the brain may include the insular cortex, the cingulate, the hypothalamus, subsets of the thalamic nuclear complex, the amygdala complex, bed nucleus of the stria terminalis, medial temporal lobe (hippocampus, parahippocampal gyrus and entorhinal cortex), elements of the basal ganglia (putamen, globus pallidus, caudate nucleus) and/or the prefrontal and/or orbital frontal cortex. Such results may be demonstrated by functional magnetic resonance imaging (fMRI) and/or suitable techniques. It is further believed that the electrical therapy signal may reduce at least one pro-inflammatory marker and/or increase at least one anti-inflammatory biomarker. Representative pro-inflammatory biomarkers include IL-1, IL-6, IL-12, IL-17, IL-18, C-reactive protein, TNF-α, and INF-γ. Representative anti-inflammatory biomarkers include IL-4, IL-10, IL-13, IFN-α, and TGF-β. The biomarkers can be assessed as part of the patient screening process, and/or at any point during the therapy regimen, described further below with reference to FIGS. 13 and 14.

As discussed above, one feature of embodiments of the current technology is that the electrical therapy signal does not generate paresthesia in the patient. Paresthesia can contaminate the benefits of neurostimulation by causing competing brain signals that detract from the desired therapeutic effects. This may occur in part because paresthesia introduces confounding information in neuroimaging analysis such as functional magnetic resonance imaging and electroencephalography. Paresthesia-inducing stimulation modulates somatosensory neural circuits instead of solely targeting vagal neural circuits, which limits the interpretation of neuroimaging results. For example, modulation of the insula (a cortical region) is commonly cited as biomarker for vagus nerve stimulation efficacy. However, the insula is also implicated in pain/noxious stimulus processing and can be modulated via somatosensory pathways. Accordingly, paresthesia-inducing stimulation can have a contaminating and/or contra-indicated impact. As a result, eliminating paresthesia from the treatment regimen can improve not only patient comfort and willingness to engage in the therapy, but also the ability of the practitioner to assess the efficacy of the therapy and make adjustment.

6.0 Representative Clinical Evaluations

Vorso Corp., the assignee of the present application, is currently conducting multiple prospective, multi-center pilot studies to research the safety, tolerability, and efficacy of devices configured in accordance with the present technology. One study is directed to patients with moderate to severe active rheumatoid arthritis, as shown in FIG. 13, and another is directed to patients with episodic migraine, as shown in FIG. 14.

Figure 13:
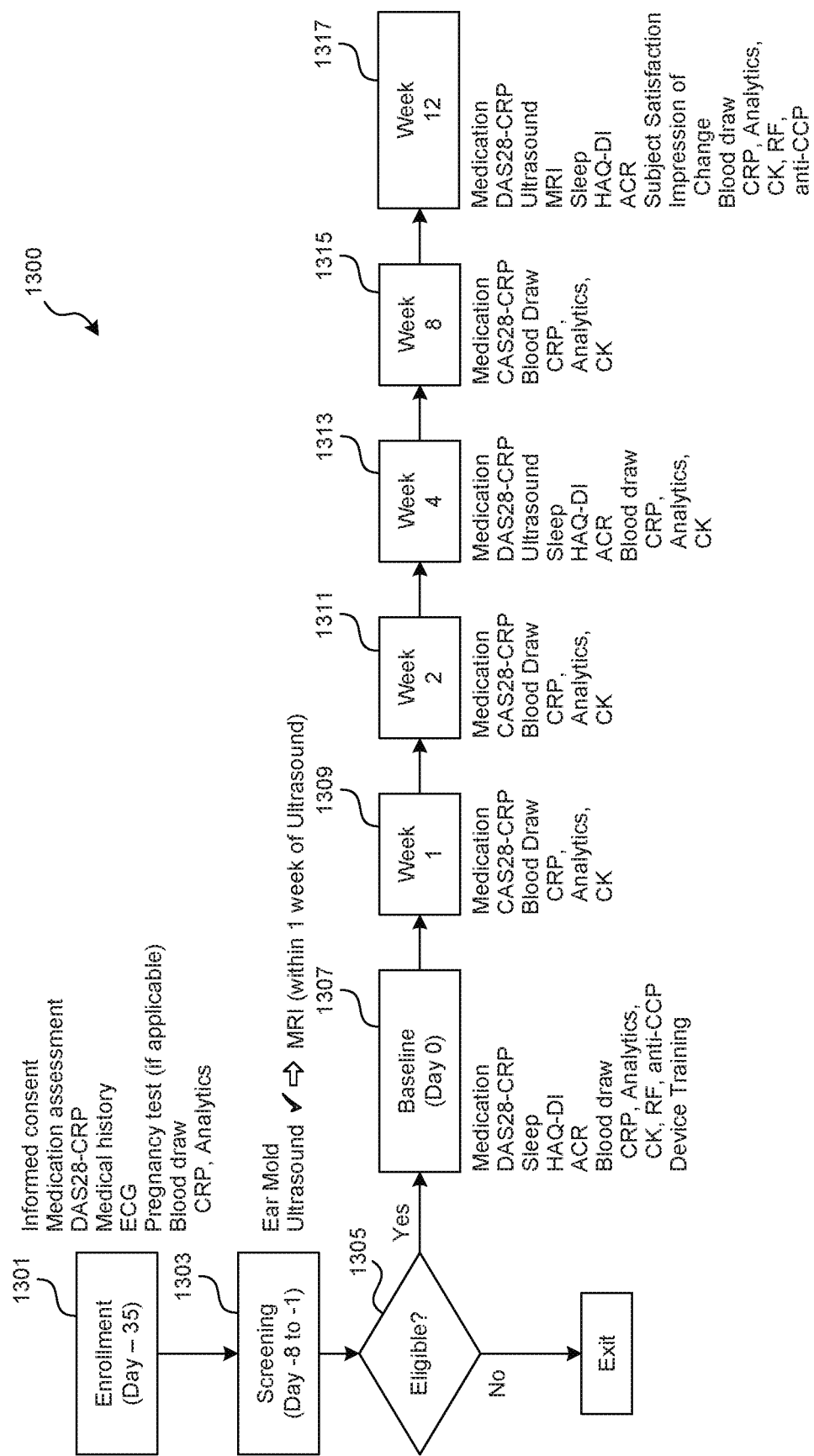
FIGS. 13 and 14 illustrate representative clinical processes for demonstrating use of the stimulation devices configured in accordance with embodiments of the present technology.
Figure 14:
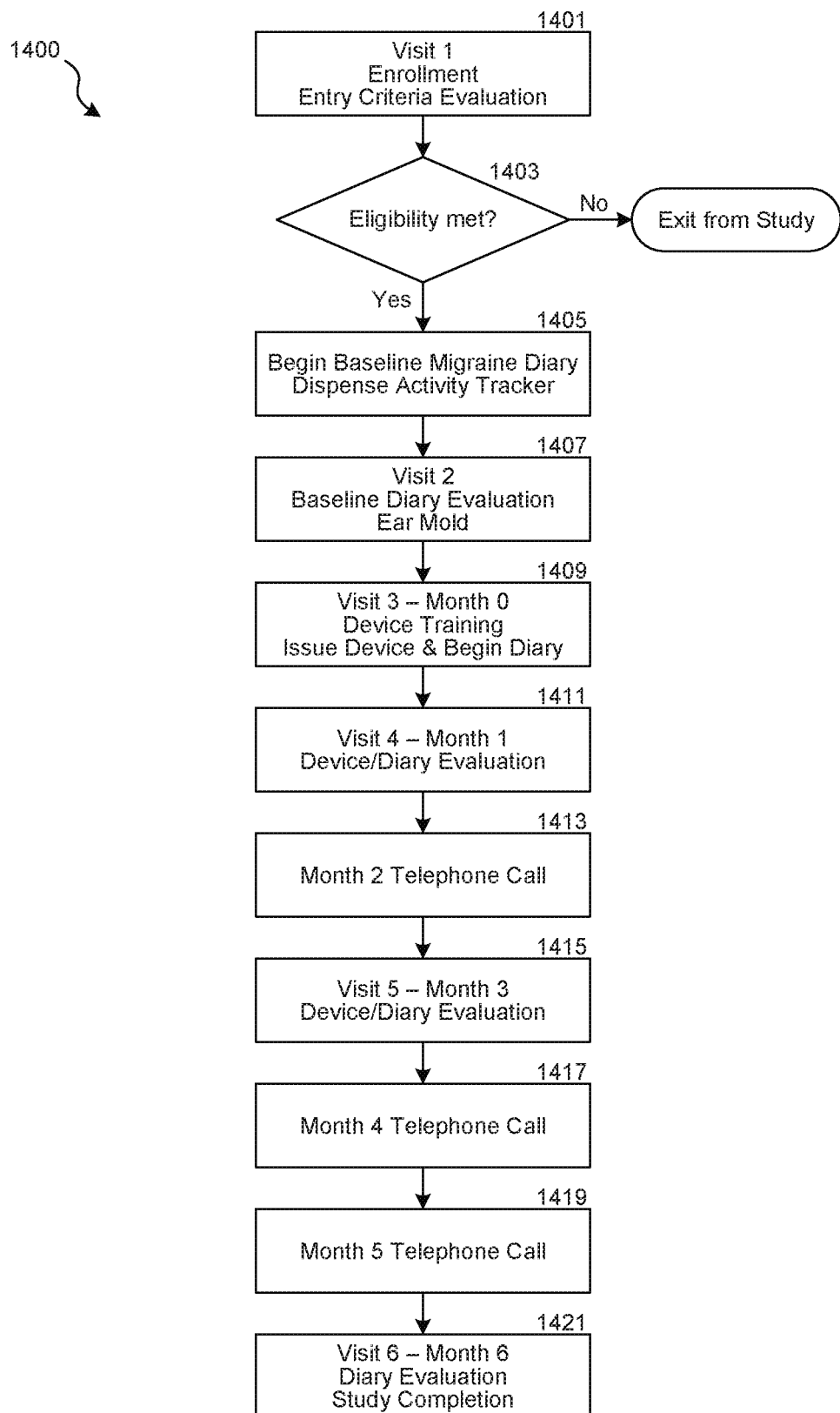

In FIGS. 13 and 14, the following acronyms are used:
DAS28-CRP (Disease Activity Score 28, using the C-Reactive Protein)
ECG (electrocardiogram)
CRP (C-Reactive Protein)
MRI (Magnetic Resonance Imaging)
HAQ-DI (Health Assessment Questionnaire Disability Index)
CK (creatine kinase)
RF (rheumatoid factor)
Anti-CCP (Anti-cyclic citrullinated peptide)

Referring first to FIG. 13, the clinical process 1300 includes an enrollment process 1301 (commencing about 35 days before treatment) and a screening process 1303 (starting at 8 days before treatment). At block 1305, based on the enrollment and screening processes, patient eligibility is determined. The inclusion/exclusion criteria for patients enrolled in the study are those who have inadequate response to DMARDs (disease-modifying anti-rheumatic drugs), and who fail one biologic treatment, or are biologic naive. The study commences (block 1307) with a number of patient metrics identified as a baseline. As indicated in FIG. 13, the metrics can include the patient's medication intake, DAS28-CRP score, the patient's sleep characteristics, HAQ-DI score, ACR, and blood characteristics (including CRP (C-reactive proteins), analytics, CK, RF, and anti-CCP). At block 1307, the patient is also trained to use the device.

The patient's progress is then tracked after one week (block 1309), two weeks (block 1311), four weeks (block 1313), eight weeks, (block 1315), and twelve weeks (block 1317). At each of the foregoing blocks, the patient metrics indicated in FIG. 13 are measured and tracked.

Early results from the study described in FIG. 13, based on changes in tender/swollen joints, patient and physician assessment scores, MRI scores, ultrasound scores and HAQ-DI changes, indicate that the therapy is safe and effective in treating patients with moderate to severe rheumatoid arthritis. The patients did not experience paresthesia or other sensory side effects. Accordingly, these preliminary results are encouraging.

Vorso Corp. is also conducting fMRI (functional MRI) studies and the early results indicate that the therapy causes functional connectivity changes in brain regions associated with the regulation of inflammation.

Referring now to FIG. 14, Vorso Corp. has also begun a study directed to safety and efficacy of devices in accordance with the foregoing description applied to patients with episodic migraine. The objective of the study is to observe and evaluate the effect of the therapy on migraine and/or associated symptoms, in subjects who suffer four to fourteen migraine days per month. As shown in FIG. 14, the clinical process 1400 includes patient enrollment (block 1401), and eligibility determination (block 1403), with the study commencing at block 1405. The primary metric during the study is the patient's migraine diary, in which the patient records migraine events. In this study, the patient undergoes a one-month baseline period, during which the patient tracks migraine activity in the absence of an electrical therapy signal. During a follow-up visit (block 1407), the baseline diary recordings are evaluated and, using an ear mold, the patient is outfitted with a custom earpiece, or two custom earpieces. At block 1409, the patient is trained to use the device. The remaining processes include evaluation at periodic intervals, including a one-month evaluation (block 1411), a two-month evaluation via telephone (block 1413), a three-month diary evaluation (block 1415), a four-month evaluation via telephone (block 1417), a five-month evaluation via telephone (block 1419), and final visit at six months (block 1421) during which the patient's diary evaluation is completed. Preliminary results are positive.

7.0 Representative Pharmacological/Biological Supplements

In at least some embodiments of the present technology, the foregoing electrical therapy signal can be provided as part of an overall treatment regimen that also includes administering a pharmacological/biological substance to the patient. It is expected that the pharmacological/biological supplement will increase the efficacy and/or duration of the electrical therapy, and/or that the electrical therapy can improve on the results obtained via a pharmacological treatment. For example, the electrical therapy signal can improve the therapeutic "window" for medication, which corresponds to the difference between efficacy and toxicity. Some of these pharmacological/biological drugs have severe dose-depending effects and it is expected that the electrical therapy can reduce the amount of drug needed by the patient and in effect limiting the side effects. In a representative example, the treatment regimen can include administering an effective amount of a pharmaceutical selected from, but not limited to, the following groups
csDMARD (conventional synthetic disease modifying antirheumatic arthritis drug) group including, but not limited to, methotrexate, sulfasalazine, leflunomide, hydroxychloroquine, gold salts;
bDMARD (biological disease modifying antirheumatic arthritis drug) group including, but not limited to, abatacept, adalimumab, anakinra, etanercept, golimumab, infliximab, rituximab and tocilizumab;

tsDMARD (targeted synthetic disease modifying antirheumatic arthritis drug) group including, but not limited to, tofacitinib, baricitinib, filgotinib, peficitinib, decernotinib and upadacitinib; and/or CGRP (calcitonin gene-related peptide) inhibitor drug group including, but not limited to, erenumab, fremanezumab, galcanezumab and Eptinezumab.

Agents useful in the treatment of asthma include inhaled corticosteroids, leukotriene modifiers, long-acting beta agonists (LABAs), theophylline, short-acting beta agonists such as albuterol, ipratropium (Atrovent®), intravenous corticosteroids (for serious asthma attacks), allergy shots (immunotherapy), and omalizumab (Xolair®).

8.0 Further Embodiments

From the foregoing, it will be appreciated that specific embodiments of the disclosed technology have been described herein for purposes of illustration, but that various modifications may be made without deviating from the technology. For example, embodiments of the earpieces described above include pairs of electrodes that deliver bipolar signals. In other embodiments, an individual earpiece can include a single, monopolar electrode, with a return electrode positioned remotely from the earpiece, or the earpiece can include more than two electrodes. The neckpiece can have configurations other than those specifically shown in the foregoing Figures. The amplitude at which the electrical therapy signal is delivered can be provided in the form of a step function that remains constant throughout the duration of the therapy, in some embodiments. In other embodiments, the amplitude of the signal can be ramped up gradually (e.g., over multiple incremental steps), for example, if the patient experiences sensory side effects, such as discomfort, when the amplitude is increased in a single step.

In addition to systems and methods for using and manufacturing such systems, the present technology includes methods for programming the systems for use. For example, as discussed above, a physician or other practitioner (e.g., a company representative), can program some or all of the signal delivery parameters into the signal generator. As was also discussed above, the patient may have the ability to modify at least some of the parameters, for example, via the external controller.

As discussed above, the communication pathways between the earpiece and the signal generator, and between the signal generator and the external controller can be in two directions. Accordingly, the signal generator can receive information from the earpieces and/or other elements of the system and take actions based on that information. In one representative example, the earpiece can include a proximity sensor that indicates if the earpiece becomes dislodged or mispositioned during a treatment session. The system can further include a small speaker or other auditory feedback element that indicates to the patient that the position of the earpiece should be adjusted. In another representative example, the external controller can track attributes of each treatment session, for example, the number of treatment sessions, the duration of the treatment sessions, the time of day of the treatment sessions and/or other data relevant to correlating the patient's response with the attributes of the treatment sessions. The system can include a wearable signal generator, e.g., in the form of a neckpiece or integrated with the earpieces (as described above), or in the form of a headband or other wearable. In a further example, the earpiece(s) can include speakers to provide music and/or other audio input to the user (e.g., via the external controller).

More generally, the system can include at least one sensor capable of sensing a body signal. The sensor may be selected from, without limitation, a cardiac sensor, a blood oxygenation sensor, a cardiorespiratory sensor, a respiratory sensor, and a temperature sensor. In one embodiment, the electrodes themselves can operate as sensors to detect proximity to the patient's skin, and/or impedance. One or more processors of the system determine a body parameter based on the body signal. For example, the processor can calculate a heart rate, heart rate variability, parasympathetic tone, sympathetic tone, or sympathetic-parasympathetic balance from a cardiac signal; a pulse oximetry value from a blood oxygenation signal; a breathing rate or end tidal volume from a respiratory signal; and/or a sleep and/or exertional level from an accelerometer, gyroscope and/or GPS device coupled to the patient's body. The system can then use the body parameter to adjust one or more parameters in accordance with which the electrical signal is delivered (or not delivered). For example, the signal may be turned off if the patient's heart rate falls below a predetermined lower limit, or if activity levels become elevated or depressed. In a representative embodiment, the sensor is located on the skin of a lateral surface of the ear (i.e., the side of the ear facing toward the patient). In another embodiment, the sensor is externally located on the skin of the patient's head below the mastoid. In still further embodiments, the sensor can be positioned at a different location, and can be carried by the earpiece(s), the neckpiece, and/or another portion of the system.

The electrical therapy signal can be applied to just a single ear, or to both ears. When therapy is applied to both ears, the signal can be the same for both, or at least one signal delivery parameter can differ for a signal applied to the right ear, as compared to a signal applied to the left ear. The signal(s) can be applied simultaneously or sequentially to each ear. In some embodiments, by using one or both ears, the system can exploit the known difference in left versus right vagus nerves as principally an inflow or outflow system of the NTS (nucleus tractus solitarius), respectively. Afferent fibers, accessible in the tragal somatic representation of the vagus as well as sympathetic afferent neural inflows, will potentially enable the therapy signals in accordance with the present technology to impact visceral sensory signal integration at higher CNS (central nervous system) structures, including the NTS, RVLN (rostroventrolateral reticular nucleus), trigeminal nucleus, locus cerelous, parabrachial nucleus, hypothalamus, subsets of the thalamus, and/or cortical structures related to autonomic functioning and/or the dorsal motor nucleus.

The therapy signal can include waveforms other than that shown in FIG. 12, e.g., a triangular waveform or a sinusoidal waveform. The therapy signal can be applied continuously (e.g., a 100% duty cycle), or in accordance with a lower duty cycle, e.g., a 50% duty cycle or other duty cycle. The signal can vary, as described above. For example, the signal can vary in an irregular, non-periodic manner, e.g., with biphasic pulses having a total duration of 50 us repeated randomly at from one microsecond to 100 microsecond intervals. In another embodiment, the irregular waveform can be characterized by the average number of zero crossing (as defined by a change in polarity) of the signal. For example, the average number of zero crossings for any given second of the stimulation signal is 40,000 for a 20 kHz signal with bi-phasic rectangular pulses. The signal can also be applied either simultaneously or alternatingly to other peripheral nerves to further enhance the therapeutic effect.

As discussed above, the patient and/or practitioner can modify therapeutic doses of stimulation through a software application (an "app") for a mobile electronic device (such as an iPhone or an Android-based mobile device) based on clinician guidelines and patients' adherence to the app. In other embodiments, the system can include verbal response options to provide patients with verbal statements about the status of the therapy, feedback, and/or instructions; the ability to modulate the maximum amplitude (and/or other parameters) of the therapy for the user based on conditioning and/or other sensor responses; monitoring the count of the therapy doses by the app (and/or system hardware); and/or enable the patient to purchase a therapy session using the app or a companion device; enable clinicians to monitor the patients' conditions and responses to therapy over the internet; and/or allowing clinicians to change the parameters of the therapy via internet-enabled communications.

Representative targets for the electrical therapy signal, in addition to or in lieu of the concha, include the antihelix, tragus, antitragus, helix, scapha, triangular fossa, lobule, and/or a lateral surface of the ear (i.e., the side of the ear facing the patient), although it is expected that stimulation provided to the concha will produce superior results.

As described above, some techniques in accordance with the present technology include coordinating the delivery of the therapy signal with the patient's respiratory cycles. Accordingly, the system can include a respiratory sensor that monitors the patient's respiratory exhalation and (a) activates the stimulator approximately at the start of each exhalation phase and (b) deactivates the stimulator approximately at the end of the each exhalation phase. The respiratory sensor can use motion or acoustic monitoring technology to identify the start and end of each exhalation phase. The respiratory sensor can be integrated in a chest or stomach belt, or integrated into a face mask. Further, the respiratory sensor can be have a band-aid-type form factor, and can placed on the patient's neck. In another configuration, the respiratory sensor can include an optical sensor, such as a photoplethysmogram (PPG) sensor that is integrated with the earpiece.

As discussed above, the disclosed electrical therapy can be applied alone or in combination with a pharmacological/biologic treatment. In other embodiments, the therapy can be combined with still further therapy types (e.g., electrical stimulation at another location of the body) in addition to or in lieu of a combination with pharmacological/biologic treatments.

Elements of the present disclosure described under a particular Heading may be combined with elements described under other Headings in any of a variety of suitable manners. To the extent any materials disclosed herein by reference conflict with the present disclosure, the present disclosure controls.

The following examples provide further representative embodiments of the present technology.

EXAMPLES

1. A system for treating a patient, comprising:
   a signal generator having instructions to generate an electrical therapy signal, at least a portion of the electrical therapy signal having:
   a frequency at or above the patient's auditory frequency limit;
   an amplitude in an amplitude range from about 0.1 mA to about 10 mA; and
   a pulse width in a pulse width range from 5 microseconds to 30 microseconds; and
   at least one earpiece having a contoured outer surface shaped to fit against the skin of the patient's external ear, external ear canal, or both, the at least one earpiece carrying at least two transcutaneous electrodes positioned to be in electrical communication with an auricular nerve of the patient.

2. The system of example 1 wherein the frequency of the electrical therapy signal is in a frequency range of about 15 kHz to about 50 kHz.

3. The system of example 1 wherein the electrical therapy signal is a non-paresthesia-generating electrical therapy signal.

4. The system of example 1 wherein the electrical therapy signal is a non-sensory response electrical therapy signal.

5. The system of example 1 wherein the at least two transcutaneous electrodes include a conductive polymer outer surface.

6. The system of example 1 wherein the signal generator includes a neckpiece positionable to be supported by the patient around the patient's neck, and wherein the system further comprises an earpiece link coupled between the neckpiece and the at least one earpiece.

7. The system of example 6 wherein the earpiece link includes at least one elongated conductor.

8. The system of example 6 wherein the at least one earpiece is removable from the earpiece link.

9. The system of example 6 wherein the earpiece link and the signal generator are contained in a unitary housing.

10. The system of example 1 wherein the at least one earpiece includes a first earpiece shaped to fit the patient's right ear and a second earpiece shaped to fit the patient's left ear.

11. The system of example 1 wherein the at least one earpiece is custom fit to the patient's ear.

12. The system of example 1, further comprising an audible feedback device coupled to the at least one earpiece to generate a feedback signal in the patient's audible frequency range.

13. The system of example 12 wherein a frequency of the feedback signal is patient-specific.

14. The system of example 1, further comprising a proximity sensor positioned to detect a location of the at least one of the electrodes relative to the patient's skin.

15. The system of example 1, further comprising an external controller configured to be in wireless communication with the signal generator.

16. The system of example 15 wherein the external controller includes a mobile device having an application for controlling the signal generator.

17. A system for treating a patient, comprising:
   a signal generator having instructions to generate an electrical therapy signal, at least a portion of the electrical therapy signal having:
   an average frequency at or above the patient's auditory frequency limit, wherein the average frequency is the inverse of the average period of the signal over multiple periods, and wherein individual periods are the sum of a first pulse width of a first pulse at a first polarity, neighboring, second pulse at a second polarity opposite the first polarity, an interphase period between the first and second pulses, and an interpulse period between the second pulse and the next pulse of the first polarity;
an amplitude in an amplitude range from 0.1 mA to 10 mA; and
a pulse width in a pulse width range from 5 microseconds to 30 microseconds; and
at least one earpiece having a contoured outer surface shaped to fit against the skin of the patient's external ear, external ear canal, or both, the at least one earpiece carrying at least two transcutaneous electrodes positioned to be in electrical communication with an auricular nerve of then patient.

18. The system of example 17 wherein the frequency of the electrical therapy signal is in a frequency range of about 15 kHz to about 50 kHz.

19. The system of example 17 wherein the electrical therapy signal is a non-paresthesia-generating electrical therapy signal.

20. The system of example 17 wherein the electrical therapy signal is a non-sensory response electrical therapy signal.

21. The system of example 17 wherein the signal generator includes a neckpiece positionable to be supported by the patient around the patient's neck, and wherein the system further comprises an earpiece link coupled between the neckpiece and the at least one earpiece.

22. The system of example 21 wherein the earpiece link includes at least one elongated conductor.

23. The system of example 21 wherein the at least one earpiece is removable from the earpiece link.

24. A method for treating a patient, comprising:
applying an electrical therapy signal to an auricular nerve of the patient via a plurality of transcutaneous electrodes carried by an earpiece positioned against the skin of the patient's external ear, external ear canal, or both; and
wherein at least a portion of the electrical therapy signal has:
a frequency at or above the patient's auditory frequency limit;
an amplitude in an amplitude range from 0.1 mA to 10 mA; and
a pulse width in a pulse width range from 5 microseconds to 30 microseconds.

25. The method of example 24 wherein the electrical therapy signal does not generate paresthesia in the patient.

26. The method of example 24 wherein the electrical therapy signal does not generate a patient-detectable sensory response.

27. The method of example 24 wherein the frequency is in a frequency range from 15 kHz to 50 kHz.

28. The method of example 24 wherein applying the electrical therapy signal causes the auricular branch of the patient's vagal nerve to generate an afferent response.

29. The method of example 24 wherein applying an electrical therapy signal includes applying the electrical therapy signal to only one of the patient's ears.

30. The method of example 24 wherein applying an electrical therapy signal includes applying at least one electrical therapy signal to both of the patient's ears.

31. The method of example 30 wherein the same electrical therapy signal is applied to both ears.

32. The method of example 30 wherein an electrical therapy signal applied to one of the patient's ears has a parameter value different than the corresponding parameter value of an electrical therapy signal applied to the other of the patient's ears.

33. The method of example 30 wherein one or more electrical signals are applied to both ears simultaneously.

34. The method of example 30 wherein one or more electrical signals are applied to both ears sequentially.

35. The method of example 24 wherein applying the electrical therapy signal causes improved connectivity between at least two regions of the patient's brain.

36. The method of example 24 wherein applying the electrical signal includes increasing the amplitude of the signal over multiple steps from a first value to a second value.

37. The method of example 24 wherein applying the electrical signal includes applying the electrical signal to address an inflammatory condition of the patient.

38. The method of example 37 wherein the inflammatory condition includes rheumatoid arthritis.

39. The method of example 24 wherein applying the electrical signal includes applying the electrical signal to address a sleep disorder of the patient.

40. The method of example 24 wherein applying the electrical signal includes applying the electrical signal to address a neurological indication of the patient.

41. The method of example 24 wherein the neurological indication include post-partum depression.

42. The method of example 24 wherein applying the electrical signal includes applying the electrical signal to enhance the patient's functioning.

43. The method of example 42 wherein the patient's functioning includes the patient's memory.

44. The method of example 24 wherein applying the electrical signal includes applying the electrical signal to address a headache and/or migraine indication of the patient.

45. The method of example 24 wherein applying the electrical signal is performed as part of a treatment regimen that also includes a pharmacological treatment of the patient.

46. The method of example 45 wherein the pharmacological treatment of the patient includes treatment with DMARD class of pharmaceutical compound.

47. The method of example 24 wherein applying the electrical signal includes applying the electrical signal over the course of at most two sessions per day.

48. The method of example 47 wherein an individual session lasts for between two seconds and 60 minutes.

49. The method of example 47 wherein an individual session lasts for between two seconds and 30 minutes.

50. The method of example 47 wherein an individual session lasts for 15 minutes.

51. The method of example 47, further comprising tracking a number of sessions.

52. The method of example 24 wherein the auricular nerve includes an auricular branch of the patient's vagal nerve.

53. A method for making a patient treatment device, comprising:
programming a signal generator to produce an electrical therapy signal, at least a portion of the electrical therapy signal having:
a frequency at or above the patient's auditory threshold;
an amplitude in an amplitude range from about 0.1 mA to about 10 mA; and
a pulse width in a pulse width range from about 5 microseconds to about 30 microseconds; and
coupling the signal generator to at least one earpiece having a contoured outer surface shaped to fit against the skin of the patient's external ear, external ear canal, or both, the at least one earpiece carrying at least two transcutaneous electrodes positioned to be in electrical communication with an auricular nerve of the patient.

54. The method of example 53 wherein the frequency is in a frequency range from about 15 kHz to about 50 kHz.

55. The method of example 53, further comprising forming the contoured outer surface of the at least one earpiece based at least in part on a patient-specific physiologic feature of the patient's ear.

56. The method of example 53, further comprising forming at least part of the at least one earpiece using an additive manufacturing technique.

We claim:

1. A system for delivering electrical signals to a person having rheumatoid arthritis, comprising:
   a signal generator having instructions to generate an electrical signal to address the person's rheumatoid arthritis, at least a portion of the electrical signal having:
      a frequency at or above the person's auditory frequency limit, wherein the frequency is in a frequency range of about 15 kHz to about 50 kHz;
      an amplitude in an amplitude range from about 0.1 mA to about 10 mA; and
      a pulse width in a pulse width range from about 5 microseconds to about 30 microseconds; and
   at least one earpiece having a contoured outer surface shaped to fit against the skin of the person's external ear, external ear canal, or both, the at least one earpiece carrying at least two transcutaneous electrodes coupled to the signal generator and positioned to be in electrical communication with an auricular nerve of the person.

2. The system of claim 1 wherein the electrical signal is a non-paresthesia-generating electrical signal or a non-sensory response electrical signal.

3. The system of claim 1 wherein the at least two transcutaneous electrodes include a conductive polymer outer surface.

4. The system of claim 1 wherein the signal generator includes a neckpiece positionable to be supported by the person around the person's neck, and wherein the system further comprises an earpiece link coupled between the neckpiece and the at least one earpiece.

5. The system of claim 4 wherein the earpiece link and the signal generator are contained in a unitary housing.

6. The system of claim 1 wherein the at least one earpiece includes a first earpiece shaped to fit the person's right ear and a second earpiece shaped to fit the person's left ear.

7. The system of claim 1 wherein the at least one earpiece is custom fit to the person's ear.

8. The system of claim 1, further comprising a proximity sensor positioned to detect a location of the at least one of the at least two transcutaneous electrodes relative to the person's skin.

9. The system of claim 1, further comprising an external controller configured to be in wireless communication with the signal generator, wherein the external controller includes a mobile device having an application for controlling the signal generator.

10. A system for delivering electrical signals to a person having rheumatoid arthritis, comprising:
    a signal generator having instructions to generate an electrical signal to address the person's rheumatoid arthritis, at least a portion of the electrical signal having:
       an average frequency at or above the person's auditory frequency limit, wherein the average frequency is the range of about 15 kHz to about 50 kHz, wherein the average frequency is the inverse of the average period of the signal over multiple periods, and wherein individual periods are the sum of a first pulse width of a first pulse at a first polarity, a neighboring, second pulse at a second polarity opposite the first polarity, an interphase period between the first and second pulses, and an interpulse period between the second pulse and the next pulse of the first polarity;
       an amplitude in an amplitude range from about 0.1 mA to about 10 mA; and
       a pulse width in a pulse width range from about 5 microseconds to about 30 microseconds; and
    at least one earpiece having a contoured outer surface shaped to fit against the skin of the person's external ear, external ear canal, or both, the at least one earpiece carrying at least two transcutaneous electrodes coupled to the signal generator and positioned to be in electrical communication with an auricular nerve of the person.

11. The system of claim 10 wherein the electrical signal is a non-paresthesia-generating electrical signal.

12. The system of claim 10 wherein the electrical signal is a non-sensory response electrical signal.

13. The system of claim 10 wherein the signal generator includes a neckpiece positionable to be supported by the person around the person's neck, and wherein the system further comprises an earpiece link coupled between the neckpiece and the at least one earpiece.

14. The system of claim 13 wherein the earpiece link includes at least one elongated conductor.

15. The system of claim 13 wherein the at least one earpiece is removable from the earpiece link.

16. The system of claim 10 wherein the interphase period is within a range from about 1 microsecond to about 10 microseconds.

17. The system of claim 10 wherein the interpulse period is within a range from about 1 microsecond to about 10 microseconds.

18. A method for delivering an electrical signal to a person having rheumatoid arthritis, comprising:
    applying the electrical signal to an auricular nerve of the person to address the person's rheumatoid arthritis, wherein the electrical signal is applied via a plurality of transcutaneous electrodes carried by an earpiece positioned against the skin of the person's external ear, external ear canal, or both; and
    wherein at least a portion of the electrical signal has:
       a frequency at or above the person's auditory frequency limit, wherein the frequency is in a frequency range from about 15 kHz to about 50 kHz;
       an amplitude in an amplitude range from about 0.1 mA to about 10 mA; and
       a pulse width in a pulse width range from about 5 microseconds to about 30 microseconds.

19. The method of claim 18 wherein the electrical signal does not generate paresthesia in the person or does not generate a person-detectable sensory response.

20. The method of claim 18 wherein applying the electrical signal causes the auricular branch of the person's vagal nerve to generate an afferent response.

21. The method of claim 18 wherein applying the electrical signal includes applying the electrical signal to only one of the person's ears.

22. The method of claim 18 wherein applying the electrical signal includes applying at least one electrical signal to both of the person's ears.

23. The method of claim 22 wherein the same electrical therapy signal is applied to both ears, and wherein (1) one or more electrical signals are applied to both ears simultaneously or (2) one or more electrical signals are applied to both ears sequentially.

24. The method of claim 22 wherein applying the at least one electrical signal includes applying a first electrical signal to one of the patient's ears and a second electrical signal to the other of the patient's ears, the first electrical signal differing from the second electrical signal with respect to one or more of frequency or amplitude.

25. The method of claim 18 wherein applying the electrical signal includes increasing the amplitude of the electrical signal over multiple steps from a first value to a second value.

26. The method of claim 18 wherein applying the electrical signal is performed as part of a treatment regimen that also includes a pharmacological treatment of the person.

27. The method of claim 26 wherein the pharmacological treatment includes treatment with a DMARD class of pharmaceutical compound.

* * * * *

UNITED STATES PATENT AND TRADEMARK OFFICE
CERTIFICATE OF CORRECTION

PATENT NO. : 10,806,928 B2
APPLICATION NO. : 16/818977
DATED : October 20, 2020
INVENTOR(S) : Vivek K. Sharma et al.

It is certified that error appears in the above-identified patent and that said Letters Patent is hereby corrected as shown below:

In the Specification

In Column 10, Line 65, delete "INF-γ" and insert -- IFN-γ --, therefor.

In Column 14, Line 51, delete "cerelous" and insert -- coeruleus --, therefor.

In the Claims

In Column 20, Line 2, Claim 10: delete "the" and insert -- in a --, therefor.

Signed and Sealed this
Sixteenth Day of March, 2021

Drew Hirshfeld
*Performing the Functions and Duties of the*
*Under Secretary of Commerce for Intellectual Property and*
*Director of the United States Patent and Trademark Office*